(12) United States Patent
Yi et al.

(10) Patent No.: US 9,949,709 B2
(45) Date of Patent: Apr. 24, 2018

(54) TECHNIQUES FOR SUPPRESSION OF MOTION ARTIFACTS IN MEDICAL IMAGING

(71) Applicants: Byong Yong Yi, Fulton, MD (US); Nilesh N. Mistry, Cary, NC (US); Xinsheng Cedric Yu, Pasadena, MD (US); Giovanni Lasio, Bel Air, MD (US)

(72) Inventors: Byong Yong Yi, Fulton, MD (US); Nilesh N. Mistry, Cary, NC (US); Xinsheng Cedric Yu, Pasadena, MD (US); Giovanni Lasio, Bel Air, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/319,604

(22) PCT Filed: Jun. 23, 2015

(86) PCT No.: PCT/US2015/037146
§ 371 (c)(1),
(2) Date: Dec. 16, 2016

(87) PCT Pub. No.: WO2015/200300
PCT Pub. Date: Dec. 30, 2015

(65) Prior Publication Data
US 2017/0156690 A1    Jun. 8, 2017

Related U.S. Application Data

(60) Provisional application No. 62/015,587, filed on Jun. 23, 2014.

(51) Int. Cl.
*A61B 6/00* (2006.01)
*A61B 6/03* (2006.01)

(52) U.S. Cl.
CPC .......... *A61B 6/5264* (2013.01); *A61B 6/032* (2013.01); *A61B 6/037* (2013.01); *A61B 6/4085* (2013.01);
(Continued)

(58) Field of Classification Search
CPC ..... A61B 6/032; A61B 6/4085; G06T 11/005; G06T 7/11; G01N 2223/419; G01N 23/046
See application file for complete search history.

(56) References Cited

U.S. PATENT DOCUMENTS 6,760,468 B1   7/2004   Yeh et al.
6,907,100 B2   6/2005   Taguchi
(Continued)

OTHER PUBLICATIONS

International Search Report and Written Opinion for the corresponding PCT Application No. PCT/US2015/037146, dated Sep. 16, 2015, pp. 1-11.
(Continued)

*Primary Examiner* — Edward Park
(74) *Attorney, Agent, or Firm* — Eugene J. Molinelli; Beusse Wolter Sanks & Maire

(57) ABSTRACT

Techniques for suppression of motion artifacts in medical imaging include obtaining projections at different times within a time interval from a medical imaging system operating on a subject. A stationary projection is determined for a first subset of the projections in which a signal source and detector array of the imaging system are in a first configuration relative to the subject. An image of the subject based on the stationary projection is displayed. For any subset, the stationary projection is a minimum value for each pixel among the subset of projections if a signal passing through a moving object of interest inside the subject is expected to cause an increase in a pixel value. Alternatively, the stationary projection is a maximum value for each pixel
(Continued)

among the subset of projections if the signal passing through the object of interest is expected to cause a decrease in a pixel value.

20 Claims, 15 Drawing Sheets

(52) U.S. Cl.
CPC .............. *A61B 6/42* (2013.01); *A61B 6/461* (2013.01); *A61B 6/50* (2013.01)

(56) References Cited

U.S. PATENT DOCUMENTS

| | | | |
|---|---|---|---|
| 7,813,783 B2* | 10/2010 | Thomas ................ | A61B 6/032 378/4 |
| 2007/0019851 A1* | 1/2007 | Nishide ................ | G06T 11/005 382/131 |
| 2010/0296751 A1 | 11/2010 | Yanai | |

OTHER PUBLICATIONS

Leng, S., et al., "Streaking artifacts reduction in four-dimensional cone-beam computed tomography," Medical Physics, 2008, pp. 1-12, vol. 35.

* cited by examiner

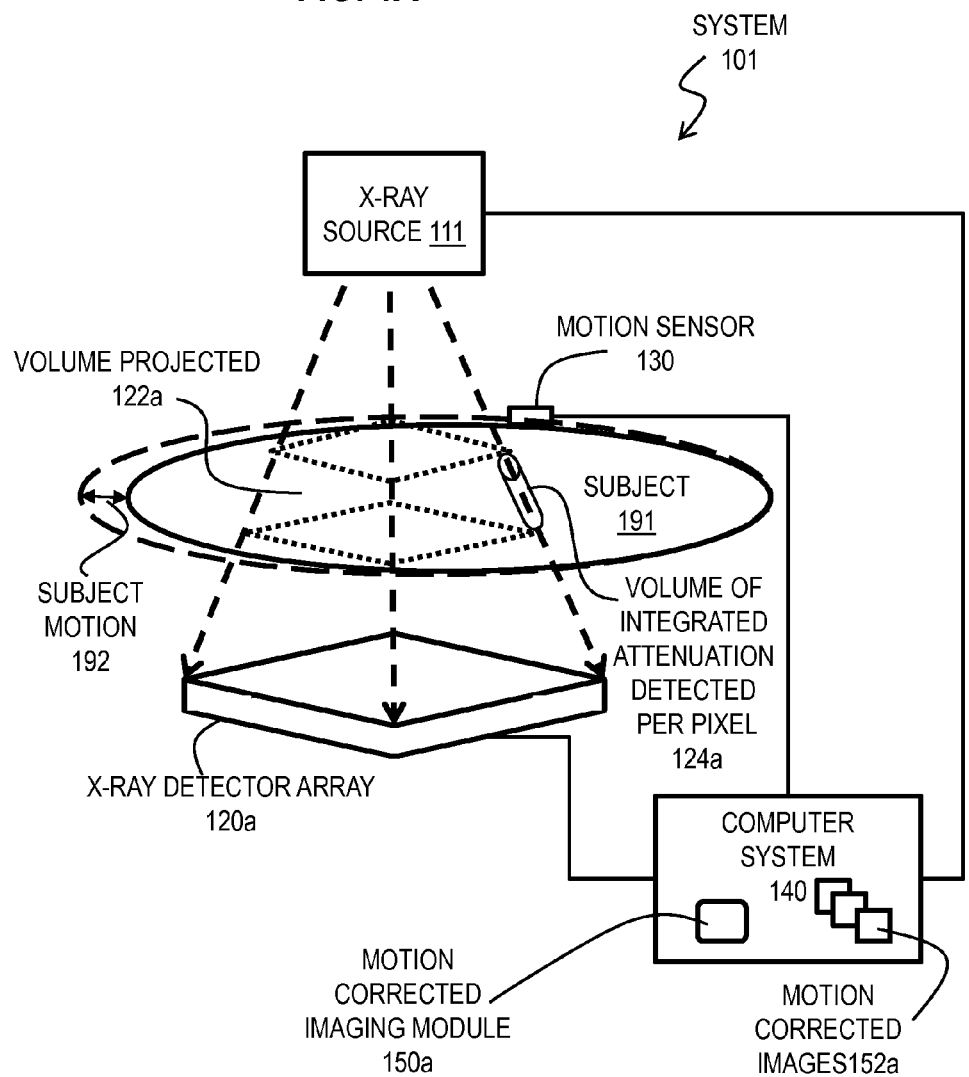

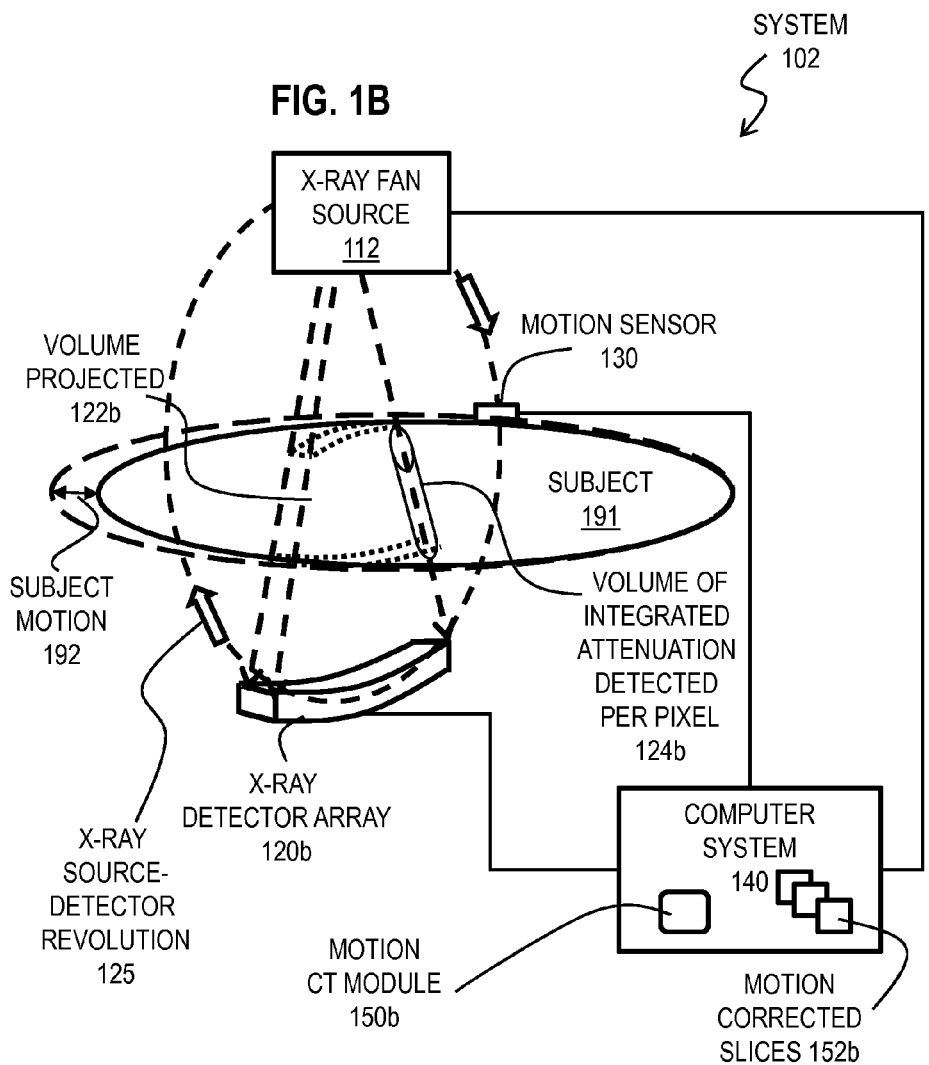
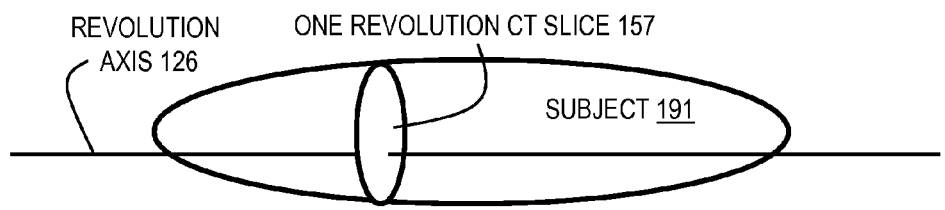

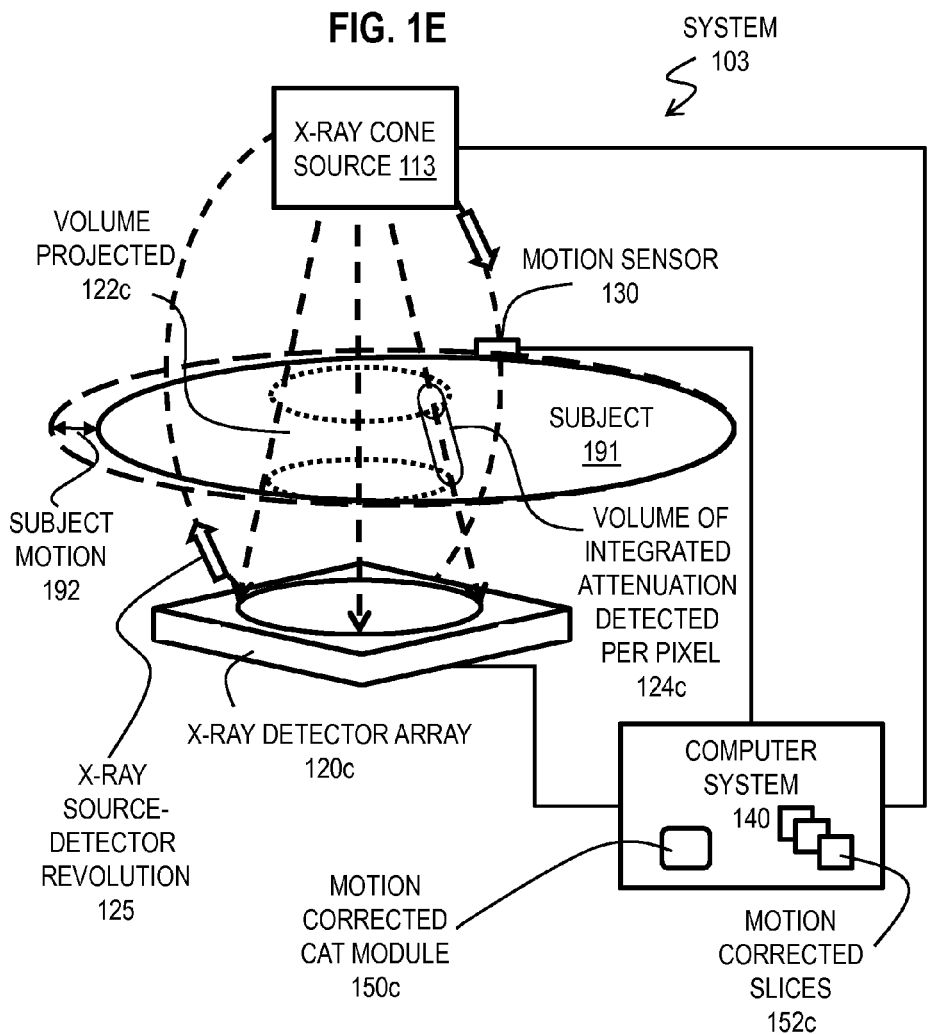
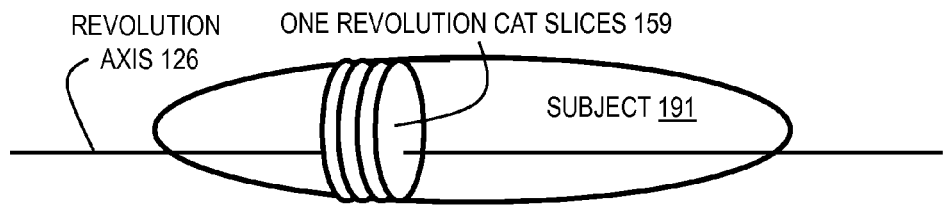

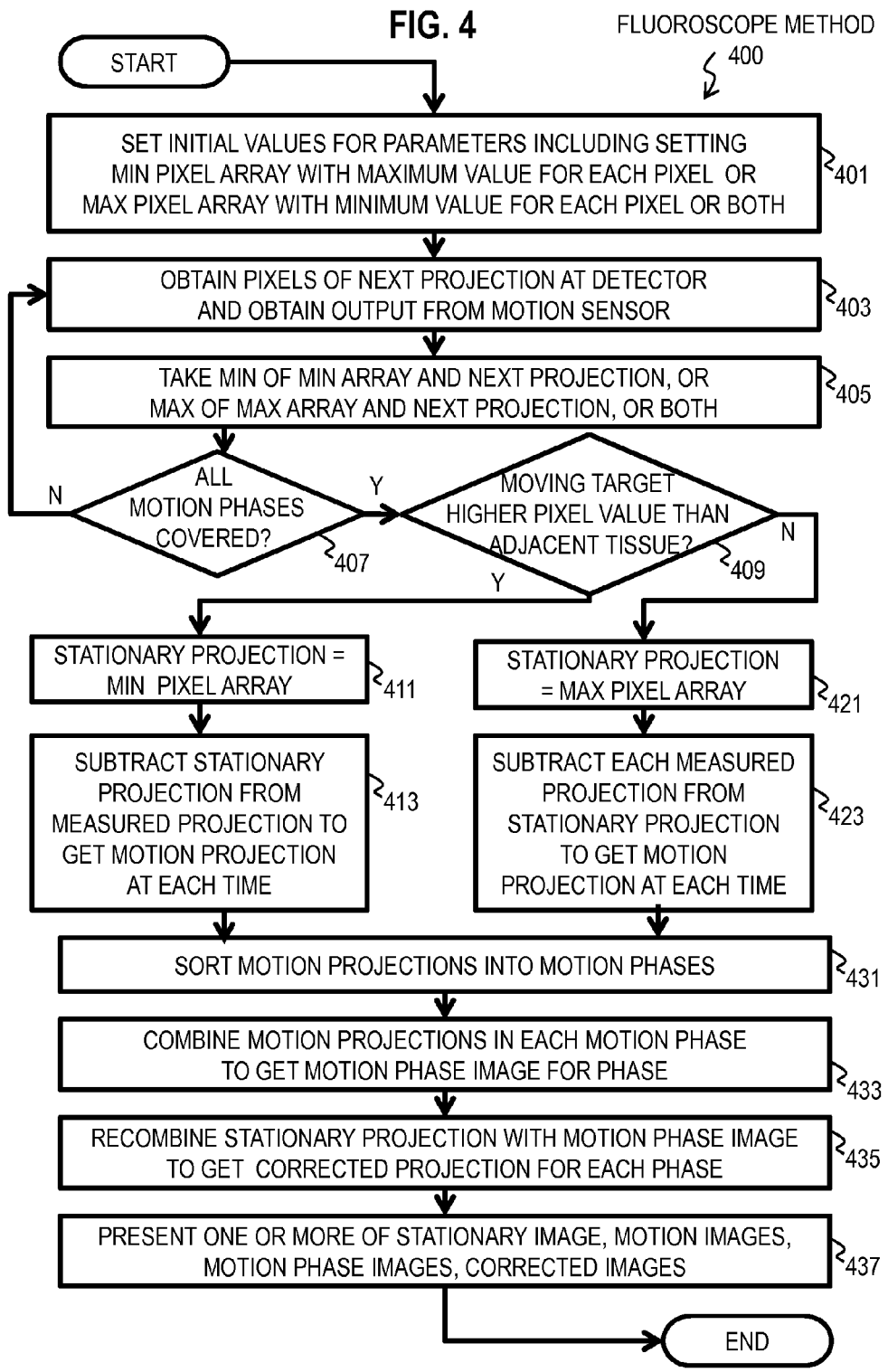

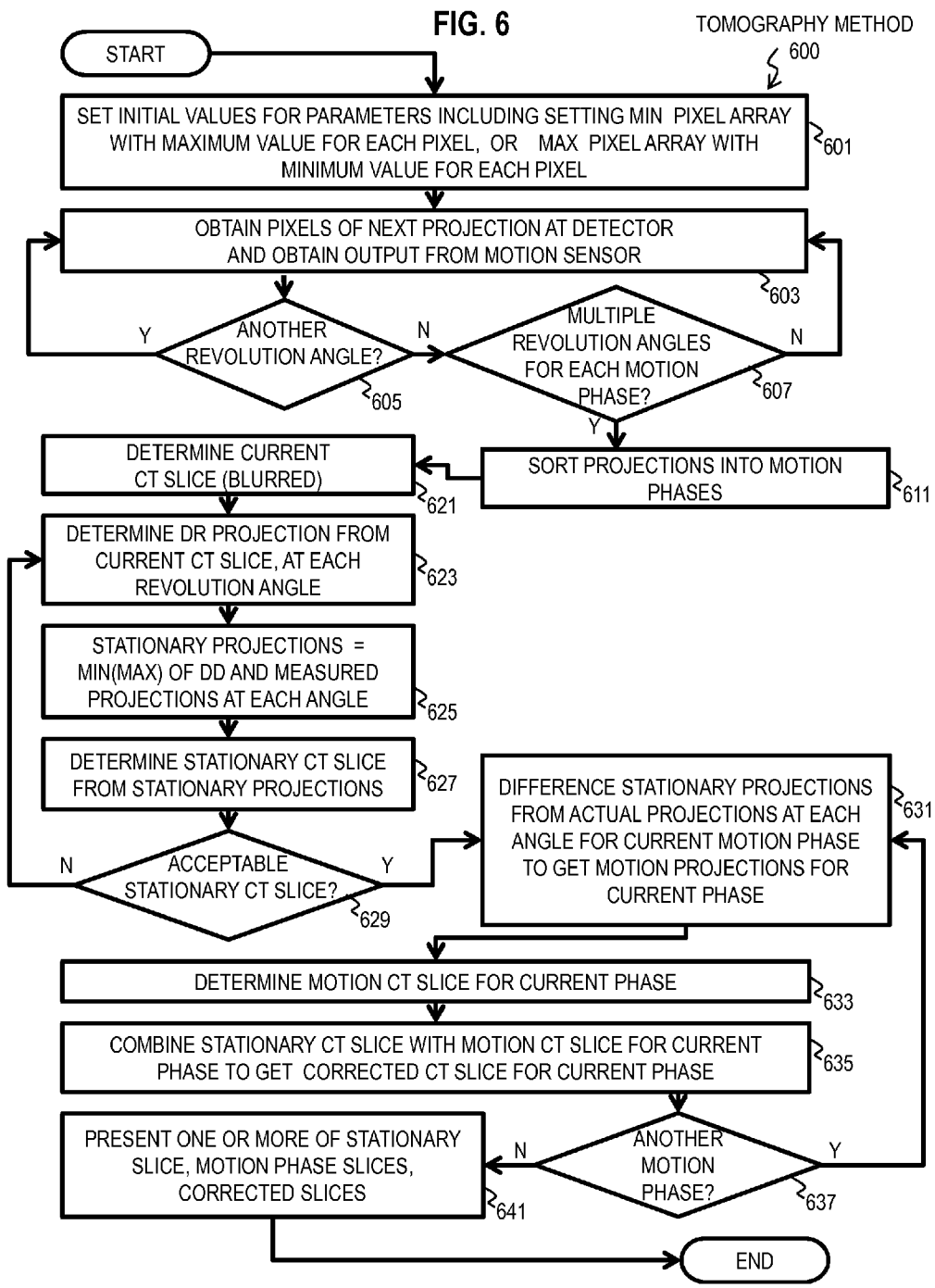

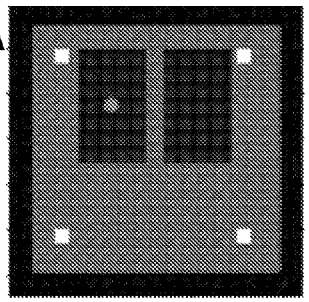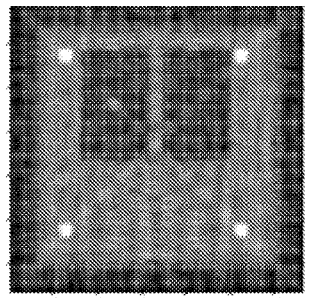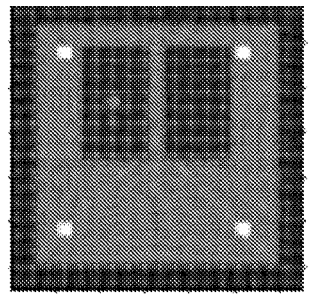
FIG.9A
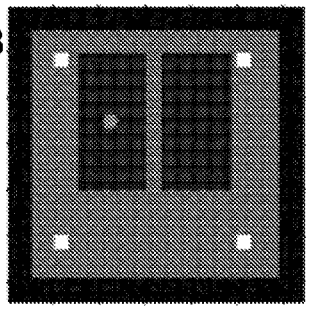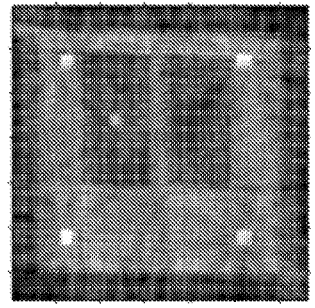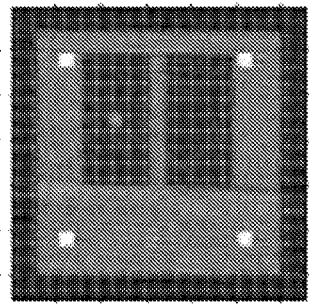
FIG.9B
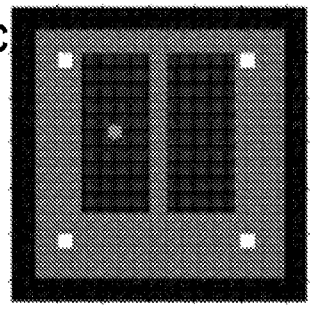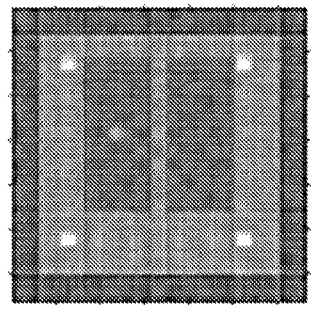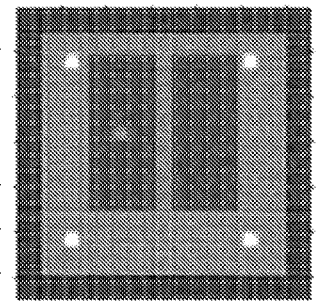
FIG.9C

US 9,949,709 B2

TECHNIQUES FOR SUPPRESSION OF MOTION ARTIFACTS IN MEDICAL IMAGING

CROSS-REFERENCE TO RELATED APPLICATIONS

This application is a 371 national stage application of PCT Application No. PCT/US2015/037146, filed 23 Jun. 2015 which claims benefit of Provisional Appln. 62/015,587, filed 23 Jun. 2014, the entire contents of which are hereby incorporated by reference as if fully set forth herein, under 35 U.S.C. § 119(e).

STATEMENT OF GOVERNMENTAL INTEREST

This invention was made with government support under Grant Number CA133539 awarded by the National Institutes of Health. The government has certain rights in the invention.

BACKGROUND

Computed tomography (CT) is a widely used technique to infer the properties of a volume interacting with a signal based on the properties of the signals that are projected through the volume at multiple different angles in one or two dimensions. CT is used with X-ray sources (either fan shaped or cone shaped), or with gamma ray sources in Positron Emission Tomography and Single Photon Emission computed Tomography (SPECT). The property measured is the attenuation of the signal as it traverses the volume of the subject. The values for the property in the inferred volume is distributed in two dimensions as slices (presented as images) or three dimensions as a series of stacked slices.

When the same volume is measured at different times, time provides a fourth dimension; and, the resulting data set is called a four dimensional (4D) data set. When the subject of the 4D CT measurement is a living animal, such as a human patient, motion of the heart and lungs and diaphragm, and tissues adjacent thereto, can confound the determination of the distribution of the property values in the volume.

For example, a concern with the irradiation of lung cancers is that many of these tumors move with respiration. Motion poses a number of special problems, including problems with accurate target definition (moving targets may appear with distorted shapes and in wrong locations on CT) and increased irradiation of normal tissues (larger fields are often used to ensure that the tumor is not missed). To improve the visualization of moving tumors, a variety of techniques have been proposed. One of the simplest is voluntary breath hold, in which the patient holds his or her breath during imaging. This is often problematic, however, in many lung cancer patients due to poor lung function. A more sophisticated approach has been implemented known as 4D computed tomography (4DCT) imaging and respiratory gating. Such periodic motions are often divided into multiple different motion phases, so that within each motion phase the position of values in the volume are relatively stable. A 4D CT scan is composed of a large number of individual CT scans obtained at various phases of the respiratory cycle. This approach allows the radiation oncologist to watch the movement of the tumor with respiration.

Reconstructing good quality images for Four-Dimensional Computed Tomography (4DCT) or Four-Dimensional Cone-Beam Computed Tomography (4D-CBCT) is always challenging especially when the data are under-sampled for each individual phase. For example, CBCT data is often acquired with limited number of projections, so that an individual motion phase may be under-sampled. Thus, while the limited number of projections is sufficient to reconstruct decent motion-averaged images; reconstructing a 4D image from this limited data leads to motion-induced artifacts. Under-sampled projection data from moving objects within a subject are reconstructed using: either a) simple filtered back projection, or b) iterative techniques that minimize or maximize some optimality criteria.

While filtered back projection is computationally efficient, using the technique with under-sampled data often leads to severe reconstruction artifacts. Iterative methods overcome this limitation by reducing the artifacts; however these techniques are computationally complex and often require either advanced reconstruction engines to handle the computational complexity or longer computation time.

SUMMARY

Techniques are provided for suppression of motion artifacts in medical imagery that do not suffer all the disadvantages of prior approaches. These techniques extract the motion components of the projection images to suppress the motion artifact and to generate the 4D reconstruction with better image quality for each slice than the reconstructed images from under-sampled projections.

In a first set of embodiments, a computer readable medium includes instructions for a processor that cause an apparatus to obtain multiple projections, at a corresponding multiple different times within a time interval, from a medical imaging system operating on a subject. Each projection includes multiple pixel values, each pixel value corresponding to a value of a signal received at a component of a detector array from a signal source after the signal passes through the subject. An object of interest potentially inside the subject is expected to move during the time interval. The instructions further cause the apparatus to determine a stationary projection for a first subset of the projections, wherein the signal source and detector array are in a first configuration (e.g., angle of revolution) relative to the subject for the first subset. The instructions further cause the apparatus to present on a display device an image of the subject based on the stationary projection. For any subset, the stationary projection includes a minimum value for each pixel among the subset of projections if a signal passing through the object of interest is expected to cause an increase in a pixel value, compared to a signal that does not. Alternatively, for any subset, the stationary projection includes a maximum value for each pixel among the subset if the signal passing through the object of interest is expected to cause a decrease in a pixel value, compared to the signal that does not.

In some embodiments of the first set, the signal source is an X-ray source and the value of the signal received at the component of the detector array indicates attenuation of the X-rays from the X-ray source. In some of these embodiments, the object of interest is a tumor and the signal passing through the object of interest is expected to cause an increase in a pixel value, so that the stationary projection is a minimum among all the projections in the subset.

In some embodiments of the first set, presenting the image of the subject based on the stationary projection includes presenting at least one of the stationary projection, or a motion image based on a difference between the stationary projection and a projection of the first subset of the plurality of projections, or a motion phase image based on one or more motion images collected during a particular motion phase when the object of interest moves periodically through multiple motion phases, or a corrected image based on the motion phase image recombined with the stationary image. In some of these embodiments, the motion phases are phases associated with breathing by the subject.

In some embodiments of the first set, wherein the plurality of projections are based on a corresponding plurality of different configurations of the signal source and detector relative to the subject, the apparatus is further caused to determine a computed tomography image directly based on the plurality of projections; and to determine multiple digitally reconstructed projections based on the computed tomography image. Each digitally reconstructed projection is based on one of the different configurations. The apparatus is further caused to determine multiple stationary projections, each based on both a digitally reconstructed projection and a projection for a corresponding configuration. The apparatus is further caused to determine a stationary computed tomography image based on the multiple stationary projections. In this embodiment, presenting an image of the subject includes presenting an image of the subject based on the stationary computed tomography image.

In some of these embodiments, presenting the image based on the stationary computed tomography image includes presenting at least one of the stationary computed tomography image; a motion projection based on a difference between a projection of the plurality of projections and a corresponding stationary projection of the multiple stationary projections; a motion phase tomography image, or a corrected tomography image, or some combination. The motion phase tomography image is based only on motion projections that occur during the particular motion phase. The corrected tomography image is based on the motion phase tomography image recombined with the stationary computed tomography image.

In some embodiments of the first set, the signal source is a gamma source disposed within the subject; and, the value of the signal received at the component of the detector array indicates a number of gamma photons from the gamma source, which is indicative of both source intensity and attenuation in the intervening tissues.

In other sets of embodiments, an apparatus or system is configured to perform the steps indicated by the above instructions. In some system embodiments, the X-ray source is a fan beam X-ray source. In other embodiments, the X-ray source is a cone beam X-ray source. In some system embodiments, the signal source is one of a Positron Emission Tomography (PET) gamma ray source or a Single-Photon Emission Computed Tomography (SPECT) gamma ray source; the signal source is configured to be injected into the subject; and, the detector array is a gamma ray detector array.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1A is a block diagram that illustrates an example X-ray fluoroscopy medical imaging system, according to an embodiment;

FIG. 1B is a block diagram that illustrates an example X-ray computed tomography (CT) medical imaging system, according to an embodiment;

FIG. 1C is a block diagram that illustrates an example single revolution slice geometry from the CT medical imaging system, according to an embodiment;

FIG. 1E is a block diagram that illustrates an example X-ray cone beam computed tomography (CBCT) medical imaging system, according to an embodiment;

FIG. 1F is a block diagram that illustrates an example single revolution slice geometry from the CBCT medical imaging system, according to an embodiment;

FIG. 4 is a flow diagram that illustrates an example method for suppressing motion artifacts in an X-ray fluoroscopy projection, according to an embodiment;

FIG. 6 is a flow diagram that illustrates an example method for suppressing motion artifacts in CT images, according to an embodiment;

FIG. 9A is a set of three images showing left to right the example lung phantom model during one motion phase, an example under-sampled computed tomography slice using only projections during that motion phase, and an example computed tomography slice for the same motion phase using the method of FIG. 6, which uses a stationary computed tomography slice based on all projections, respectively, according to an embodiment;

FIG. 9B and FIG. 9C are like FIG. 9A but for two different motion phases, according to an embodiment;

DETAILED DESCRIPTION

Figure 1D:
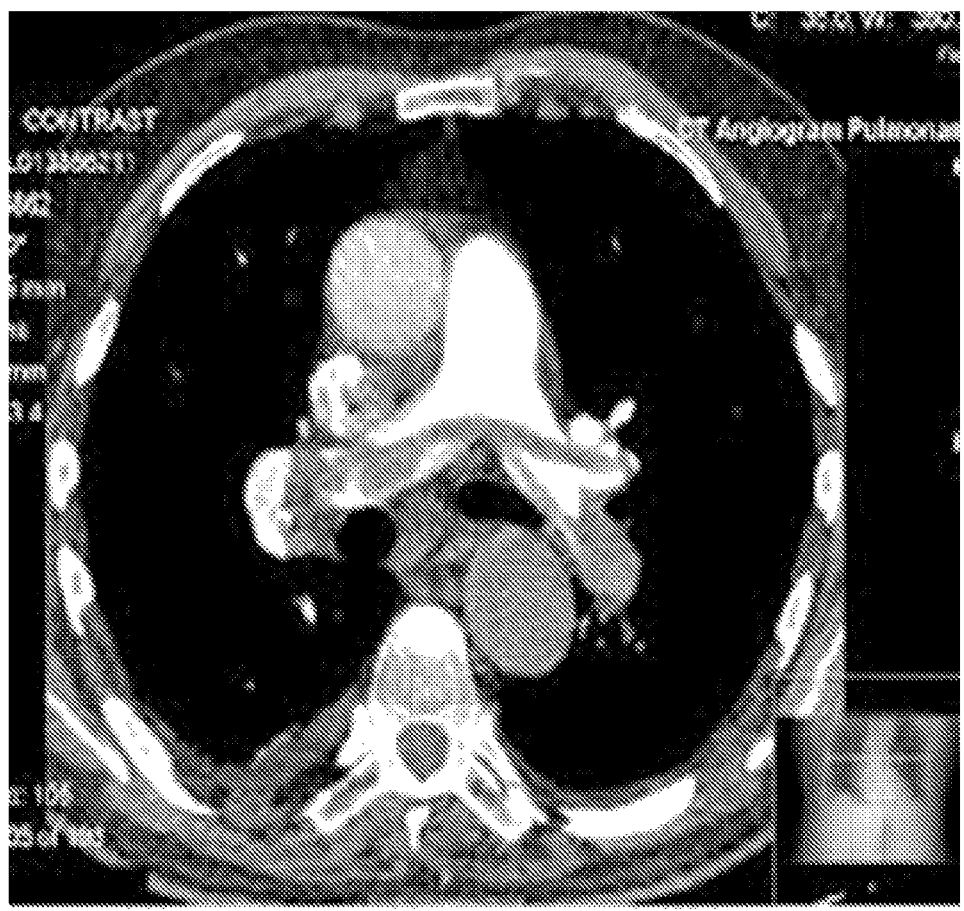
FIG. 1D is an image that illustrates an example slice from a CT medical imaging system, according to an embodiment.

Techniques are described for suppression of motion artifacts in medical imaging. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of X-ray CT imaging with a movement of a dense tissue located in a lung subject to periodic movement. However, the invention is not limited to this context. In other embodiments, less dense tissue or a gas pocket is moving due to breathing, or a feature is moving with a beating heart, or other features are imaged during patient tremors or other non-periodic movement. In some embodiments gamma ray CT imaging is used as in positron emission tomography (PET) or single particle emission computed tomography (SPECT) medical imaging systems of the heart or lung or adjacent tissue or other tissue subject to periodic or non-periodic movement.

FIG. 1A is a block diagram that illustrates an example X-ray fluoroscopy medical imaging system 101, according to an embodiment. Although a subject 191 of the imaging system 101 is depicted for the purposes of illustration, the subject 191 is not part of the system 101. The system 101 includes an X-ray source 111 and X-ray detector array 120a disposed on opposite sides of a support structure (not shown) for supporting the subject 191. A controller such as computer system 140, as described in more detail below with reference to FIG. 10, controls operation of the X-ray source 111 and collection of data from the X-ray detector array 120a. X-rays emitted from the source 111 are depicted as short dashed arrows which penetrate the subject and strike the detector array 120a, on which each array element makes a separate measurement of X-ray intensity. These measurements are usually depicted as an image with each array element presented as a picture element (pixel) of the image; and the image is called a projection image, or, more simply a projection. Thus the terms "pixel" and "detector array element" are used interchangeably herein, but the different usage should be clear from the context, The intensity measured at each array element is attenuated by the absorption and scattering of x-rays in the subject 191. While different parts of the subject, such as different tissues in a patient, may absorb and scatter the x-ray energy differently, what is detected by each detector array element is the integrated attenuation through volume 124a. The total volume affecting the projection image is shown as volume projected 122a within the subject 191 and between the dotted areas on a top surface and bottom surface of the subject.

Movement by the subject, such as movement of the head and chest during breathing, is indicated in FIG. 1A by two outlines for the subject 191, a solid outline representing one phase of the subject's motion and a long dashed outline representing a different phase of the subject's motion. An arrow connecting the two outlines indicates subject motion 192. As a result of such motion during collection of the measurements at the detector array 120a, the projection image becomes somewhat blurred. The movement phase at any time is determined by a motion sensor 130, which reports motion by the subject to the computer system 140.

According to various embodiments, a motion corrected imaging module 150a takes the measurements from the x-ray detector array at each of several different times; and removes or suppresses the effects of the motion 192 to produce a series of motion corrected images 152a in one or more data structures. In the depicted embodiment, the module 150a and motion corrected images 152 are located in the computer system 140 serving as controller for x-ray source 111 and data acquisition system for x-ray detector 120a.

Although processes, equipment, and data structures are depicted in FIG. 1A, and following figures, as integral blocks in a particular arrangement for purposes of illustration, in other embodiments one or more processes or data structures, or portions thereof, are arranged in a different manner, on the same or different hosts or other equipment, in one or more databases, or are omitted, or one or more different processes or data structures are included on the same or different hosts or equipment. For example, in other embodiments, the module 150a, or images 152 or both are located on one or more other devices or are implemented on a chip set such as described in more detail below with reference to FIG. 11.

Various x-ray detectors are well known. Indirect detectors contain a layer of scintillator material, either gadolinium oxysulfide or cesium iodide, which converts the x-rays into light. Due to the impracticability of focusing x-rays, the sensors have exactly the same size as the image they capture. Directly behind the scintillator layer is an amorphous silicon-on glass detector array manufactured using a process very similar to that used to make liquid crystal display (LCD) televisions and computer monitors. Like a thin film transistor (TFT)-LCD display, millions of roughly 0.2 millimeter (mm, 1 mm=$10^{-3}$ meters) pixels each containing a thin-film transistor form a grid patterned in amorphous silicon on the glass substrate. Unlike an LCD, but similar to a digital camera's image sensor chip, such as a charge-coupled device (CCD), each pixel also contains a photodiode which generates an electrical signal in proportion to the light produced by the portion of scintillator layer in front of the pixel. The signals from the photodiodes are amplified and encoded by additional electronics positioned at the edges or behind the sensor array in order to produce an accurate and sensitive digital representation of the x-ray image.

Flat panel detectors (FPDs) such as Amorphous selenium (a-Se) FPDs are known as "direct" detectors because X-ray photons are converted directly into charge. The outer layer of the flat panel in this design is typically a high-voltage bias electrode. X-ray photons create electron-hole pairs in a-Se, and the transit of these electrons and holes depends on the potential of the bias voltage charge. The charge pattern is then read by a thin-film transistor (TFT) array in the same way images produced by indirect detectors are read.

During the X-ray fluoroscopy on a subject, the detector array acquires a series of "images" at a corresponding series of times. An image comes as a function (called an image function) describing the signal produced, during the exposure time, by the x-ray beam at each of the elements of the detector array. The detector array may have a certain number of elements (e.g. 1000×500). Each array element is identified by its rank/position in the rows and columns of the detector array. Thus an image is defined by the projection function P=P(x, y); where x is one of $\{x_1, \ldots, x_{max}\}$; y is one of $\{y_1, \ldots, y_{max}\}$, and "P" is the signal (or analogous value) at a pixel corresponding to a detector array element. For example, the analogous value of attenuation is taken to be large where the intensity at the detector array element is small, so the analogous attenuation signal projection P is derived by subtracting the intensity at the array element from the maximum intensity received from the source, e.g., when the subject is not in place. In various embodiments, the projection P can be defined in terms of either transmittance or attenuation. The transmittance is the ratio of the intensity measured by the detector with the subject in place vs the measurement when it is not in place. The attenuation is normally defined in this context as −log(transmittance). In fluoroscopy lower transmittance is represented with high image brightness, with the use of an appropriate lookup table for conversion to grayscale. This is why bones appear white and lower attenuation areas like air appear black. The method of performing fluoroscopy includes acquiring a series of "n" projections P1(x, y); P2(x, y) . . . Pn(x, y) at the times t1, t2, . . . , tn.

Any motion sensor may be used as motion sensor 130. In various embodiments the motion sensor includes one or more of the following. In some embodiments, one or more reflective markers are used. Each reflective marker is placed on the patient, on a moving part of the anatomy deemed representative of the imaged anatomy's motion. In some embodiments, the marker is reflective in the infrared and an infrared camera acquires continuously frames of the marker. In o other embodiments, a high contrast visible marker is used and an ordinary video camera is used to acquire the frames. From these frame, the motion pattern of the marker is measured and recorded. In some embodiments, the motion of an implanted marker is measured by the x-ray imaging itself, or by electromagnetic array tracking, if the marker is a beacon coil, as in the Calypso system from Varian of palo Alto, Calif. In some embodiments, abdominal motion is monitored by placing a rubber air bellows around the waist. The bellows is attached to a pressure transducer. As the abdomen shrinks and expands, the transducer measures the air pressure changes within the bellows; the signal is digitized and recorded, and constitutes the breathing waveform.

FIG. 1B is a block diagram that illustrates an example X-ray computed tomography (CT) medical imaging system 102, according to an embodiment. Although a subject 191 of the imaging system 102 is depicted for the purposes of illustration, the subject 191 is not part of the system 102. Subject motion 192 and motion sensor 130 are as described above.

The system 102 includes an X-ray fan source 112 and a narrow X-ray detector 120b disposed on opposite sides of a support structure (not shown) for supporting the subject 191. The narrow X-ray detector array 120b is shaped with a large number of elements in one dimension and a few elements in the perpendicular dimension in order to match the fan beam output by the fan beam X-ray source 112. In some embodiments the narrow detector is a line detector with a single row of detector array elements. A controller such as computer system 140, as described in more detail below with reference to FIG. 10, controls operation of the X-ray source 112 and collection of data from the X-ray detector array 120b. X-rays emitted from the source 112 are depicted as short dashed arrows which penetrate the subject and strike the detector array 120b, on which each array element makes a separate measurement of X-ray intensity.

As described above, what is detected by each detector array element is the integrated attenuation through volume 124b. The total volume affecting the projection image is shown as volume projected 122b within the subject 191 and between the dotted areas on a top surface and bottom surface of the subject.

The Radon transform is the integral transform consisting of the integral of a function over straight lines (e.g., the integral of X-ray attenuation or gamma ray attenuation or intensity on rays straight through the subject volume 124b as measured at each detector array element). The transform was introduced in 1917 by Radon, who also provided a formula for the inverse transform. The Radon transform is widely applicable to tomography, the creation of an image associated with cross-sectional scans of an object from the projection data. If a function $f$ represents an unknown density (e.g., signal attenuation per unit length), then the Radon transform represents the projection data obtained on a detector array, such as detector array 120b. Hence the inverse of the Radon transform can be used to reconstruct the original density from the projection data, and thus it forms the mathematical underpinning for tomographic reconstruction, also known as image reconstruction. The inverse Radon transform uses the projection through the same space (slice or volume) in many different directions to reconstruct the distribution off (e.g., signal attenuation) in the space. The series of projection images through the space, when plotted end to end, form a sinogram. The sinogram is input to the inverse Radon transform to produce the distribution of the density $f$ inside the space. Efficient implementations of the inverse Radon transform, as describe by Radon, Johann, "On the determination of functions from their integral values along certain manifolds," Medical Imaging, IEEE Transactions on, vol. 5, no. 4, pp. 170, 176, December 1986 doi: 10.1109/TMI.1986.4307775, are well known and used in tomography, e.g., as functions in MATLAB™ from The MATHWORKS™ Inc., of Natick, Mass., and need not be described in detail here.

Thus to utilize the inverse Radon transform to deduce the distribution of signal attenuation within the space, a large number of projections through the space is desirable. To achieve this large number of projection angles in X-ray computed tomography, the x-ray fan beam source 112 and the matching x-ray receiver 120b are mounted to revolve around the subject 191 in an x-ray source-detector revolution direction 125. These projections are again represented by the notation introduced above for fluoroscopy and includes acquiring a series of "n" projections P1(x, y); P2(x, y) . . . Pn(x, y) at the times t1, t2, . . . , tn, with corresponding angles θ1, θ2, . . . θn.

FIG. 1C is a block diagram that illustrates an example single revolution slice geometry from the CT medical imaging system 101, according to an embodiment. The X-ray attenuation at each position on CT slice 157 is obtained by one revolution of the x-ray source 112 and detector 120b around subject 191, the acquisition of multiple projections at different angles, and application of the inverse Radon transform. The above angular and projection information is used to construct a 2D image ("a slice") of the imaged subject represented by I(i, j). Here (i, j) are the coordinates of the imaged slice with respect to an axis of revolution of the CT scanner The axis of the revolution 126 need not be aligned with a center axis of the subject 191. Because the x-ray source 112 and receiver 120b revolve around this axis 126, the slice I(i, j) is also called a computed axial tomography (CAT) slice or CAT scan image.

FIG. 1D is an image that illustrates an example computed tomography slice I(i, j) from a CT medical imaging system, according to an embodiment. The distribution of different x-ray attenuation values inside the subject is revealed using the multiple projections of x-rays through the subject. The subject 191 is then moved in the axial direction relative to the revolving source 112 and detector array 120b to obtain another slice at another axial location. Gradually a rather large volume or the entire subject can be scanned.

Because each projection is taken at a different time and the subject introduces subject motion 192, the CT slice I(i, j) can include various motion artifacts, such as different density errors in different directions.

According to various embodiments, a motion corrected imaging module 150b takes the measurements from the x-ray detector array at each of several different times and angles; and removes or suppresses the effects of the motion 192 to produce a series of motion corrected slices 152b in one or more data structures. In the depicted embodiment, the module 150b and motion corrected images 152b are located in the computer system 140 serving as controller for x-ray source 112 and data acquisition system for x-ray detector 120b. In other embodiments either or both of module 150b and slices 152b are arranged in a different manner, such as on chip set described below with reference to FIG. 11 on one or more other devices.

Although a fan beam source 112 and narrow x-ray detector array 120b are depicted, in other embodiments a different shaped beam source and detector array shape are used. For example, a pencil beam can be used with a small array or single element detector. However, the fan beam is a common configuration and more rapidly acquires the number of different angle projections desirable for the tomographic reconstruction of each slice. FIG. 1E is a block diagram that illustrates an example X-ray cone beam computed tomography (CBCT) medical imaging system 103, according to an embodiment. This system 103 acquires the desirable projections for tomographic reconstruction even faster and can determine many more slices per revolution than the fan beam system 102. Although a subject 191 of the imaging system 103 is depicted for the purposes of illustration, the subject 191 is not part of the system 103. Subject motion 192 and motion sensor 130 are as described above.

The system 103 includes an X-ray cone beam source 113 and wide X-ray detector 120c disposed on opposite sides of a support structure (not shown) for supporting the subject 191. The X-ray detector array 120c is shaped with a large number of elements in two dimensions in order to match the cone beam output by the cone beam X-ray source 113. A controller such as computer system 140, as described in more detail below with reference to FIG. 10, controls operation of the X-ray source 113 and collection of data from the X-ray detector array 120c. X-rays emitted from the source 113 are depicted as short dashed arrows which penetrate the subject and strike the detector array 120b, on which each array element makes a separate measurement of X-ray intensity.

As described above, what is detected by each detector array element is the integrated attenuation through volume 124c. The total volume affecting the projection image is shown as volume projected 122c within the subject 191 and between the dotted areas on a top surface and bottom surface of the subject. These projections are again represented by the notation introduced above for fluoroscopy and fan beam imaging systems and includes acquiring a series of "n" projections P1(x, y); P2(x, y) . . . Pn(x, y) at the times t1, t2, . . . , tn, with corresponding angles θ1, θ2, . . . θn.

As described above, to utilize the inverse Radon transform to deduce the distribution of signal attenuation within the space of volume 122c, a large number of projections through the space is desirable. To achieve this large number of projection angles in x-ray computed tomography, the x-ray cone beam source 113 and the matching x-ray receiver 120c are mounted to revolve around the subject 191 in an x-ray source-detector revolution direction 125. The above angular and projection information is used to construct several 2D images ("slices") of the imaged subject, each slice represented by I(i, j) as described above for a fan beam CT imaging system 102. FIG. 1F is a block diagram that illustrates an example single revolution slice geometry from the CBCT medical imaging system 103, according to an embodiment. The X-ray attenuation at each position on CT slices 159 (also called CAT scan images) is obtained by one revolution of the x-ray source 113 and detector 120c around subject 191, the acquisition of multiple projections at different angles, and application of the inverse Radon transform. The axis of the revolution 126 is as described above. As described above, the subject 191 is then moved in the axial direction relative to the revolving source 113 and detector array 120c to obtain another slice at another axial location with or without overlap and therefor redundant slices at previously sampled axial locations.

Because each projection is taken at a different time and the subject introduces subject motion 192, the CT slices 159 can include various motion artifacts, such as different density errors in different directions.

According to various embodiments, a motion corrected imaging module 150c takes the measurements from the x-ray detector array 120c at each of several different times and angles; and removes or suppresses the effects of the motion 192 to produce a series of motion corrected slices 152c in one or more data structures. In the depicted embodiment, the module 150c and motion corrected images 152c are located in the computer system 140 serving as controller for x-ray source 113 and data acquisition system for x-ray detector 120c. In other embodiments either or both of module 150c and slices 152c are arranged in a different manner, such as on chip set described below with reference to FIG. 11 on one or more other devices.

As stated above, subject motion 192 (such as heart beats, breathing and non-periodic tremors) introduces motion artifacts into projections and slices inferred from the measurements at detector arrays 120a, 120b and 120c. For example, if projections acquisition is performed during a respiratory cycle, typically the subject breathes multiple times during the acquisition.

Figure 2:
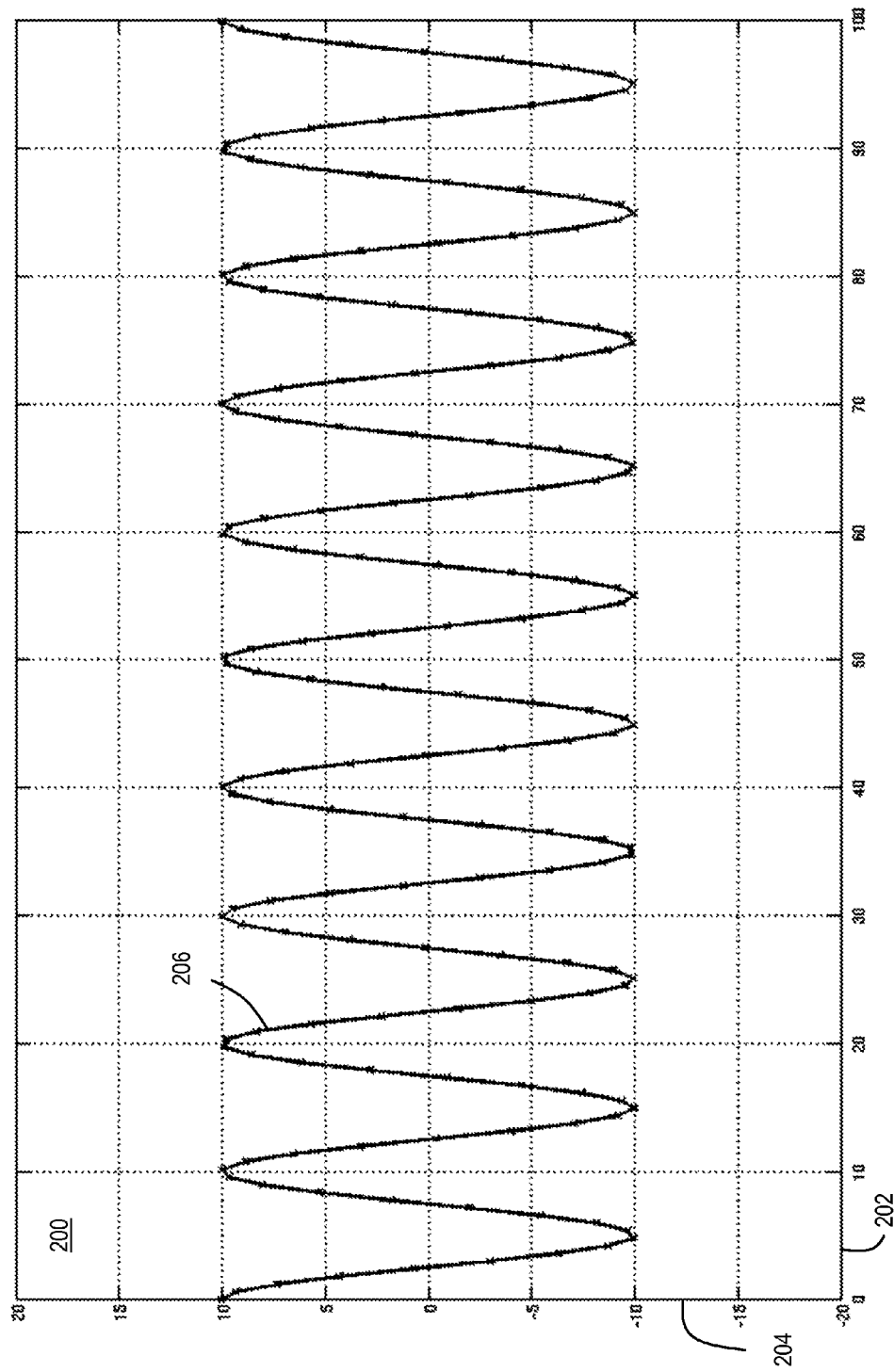
FIG. 2 is a graph that illustrates example periodic breathing motion phases, according to an embodiment.
Figure 10:
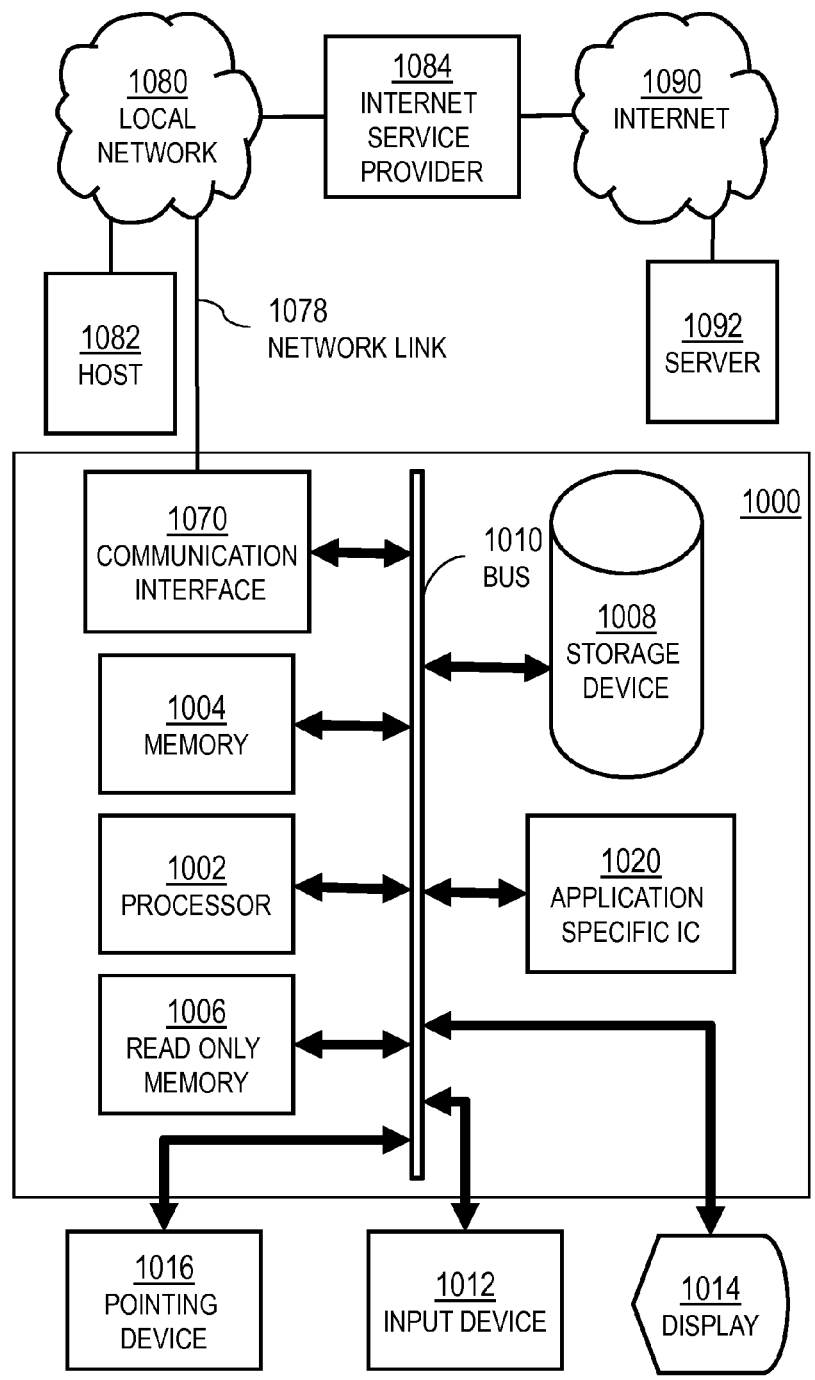
FIG. 10 is a block diagram that illustrates a computer system upon which an embodiment of the invention may be implemented.

To illustrate this point, it is assumed that the subject breaths 36 times during one revolution over 360 degrees, one breath every ten degrees. FIG. 2 is a graph that illustrates example periodic breathing motion phases, according to an embodiment. The horizontal axis indicates angle of revolution in degrees which is related to time by rate of revolution; and, the vertical axis indicates chest displacement as detected by motion sensor 130, in arbitrary units. Only ten of the 36 breathing cycles (thus only 100 degrees of the 360 degrees in a complete revolution) are depicted in FIG. 10. Trace 206 depicts the subject motion 192. The angle at which a projection is collected at the detector array (120b or 120c) is marked by dots on trace 206. There are about 16 such projections per breathing cycle, corresponding to about 1.6 projections per degree and about 600 projections over 360 degrees. Clearly some projections are collected at peak displacement of 10 units (full lungs), and some at valley displacement of −10 units (full exhale) of the movement, while other projections are collected during inhale and exhale with displacements between −10 and +10 units. The displacement can be grouped into different motion phases, such as displacement bins of −10 to −9, −9 to −7, −7 to −5, . . . , 5 to 7, 7 to 9, and 9 to 10. In some embodiments, the bins between −9 to +9 units are split into two different bins representing inhale and exhale phases. This is an amplitude binning approach.

Some embodiments use a phase binning approach. A phase binning approach starts by setting the number of desired bins. Then the peak inhale points are identified and defined as the "0%" phase. The times of the other phases are calculated taking the time difference between peaks and selecting the time points that fall at a given phase percentage such as 25%, 50% and 75%, where. 75% is three quarters of the time between the 0% phase peaks.

Clearly, the number of projections in one motion phase are much reduced compared to the total number of projections. For the 11 phases described above there is an average of about 55 projections per motion phase, with more falling in the bins with slow change at peaks and valleys (9 to 10 units, positive or negative) and fewer in bins for motion phases with rapid change, such as in the bin from −1 to +1 units. In general, the motion phases are under-sampled for performing a tomography reconstruction of a cross sectional slice (also called a CAT scan image).

1. Overview

Figure 3:
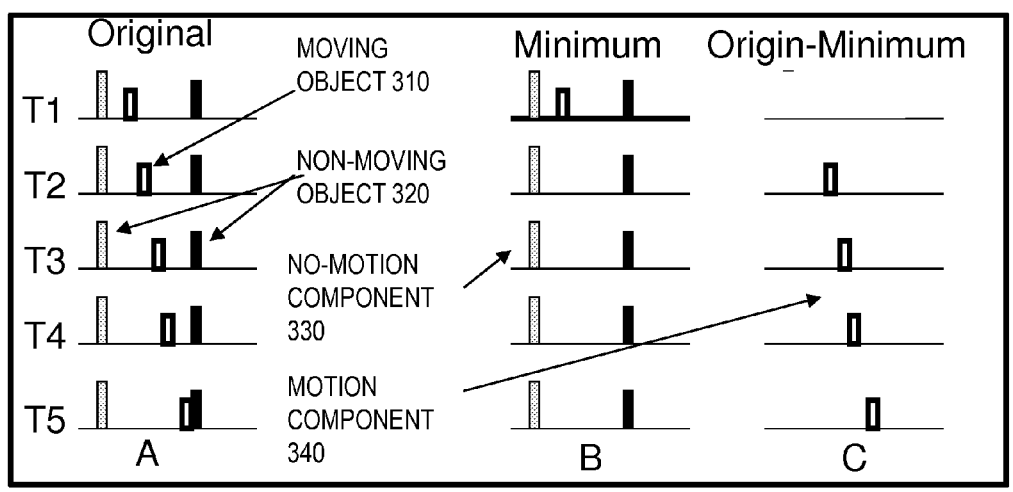
FIG. 3 is a block diagram that illustrates an example use of a minimum operation to remove motion effects, according to an embodiment.

Here are introduced techniques that extract the motion components of the projection images to suppress the motion artifact and to generate fluoroscopy images and 3D to 4D tomography reconstructions with better image quality than uncorrected images or reconstructed slices from under sampled projections. FIG. 3 is a block diagram that illustrates an example use of a minimum operation to remove motion effects, according to an embodiment. The first column (column A) represents pixel values along one row of detector array elements at five different times (T1 through T5) in an idealized example to illustrate the principle of operation. This is the original projection data for this idealized example. There are two non-moving objects 320 that retain the same measured intensity at the same pixels in all five projections. There is a moving object 310 that retains the same measured intensity but at different pixels in the five projections. While an object one pixel wide could be detected in the same way, it is here assumed that each of the moving and non-moving objects is evident in multiple adjacent pixels. It is further assumed that the values are attenuation values (not received X-ray intensity) and are plotted relative to background or average tissue attenuation and not relative to zero attenuation.

With these assumptions, a minimum operation on each pixel among all the received projections can remove the moving object and provide a projection image of just the stationary objects, called a stationary projection hereinafter. The pixels after the minimum operation are depicted in the second column (column B) of FIG. 3 and marked "Minimum." For example, after the first projection the minimum operation leaves each pixel value unchanged. But after the second protection at time T2, the moving object appears only in different pixels, and is removed by the minimum operation, which leaves the pixel values for the two non-moving objects. The minimum is unchanged by the projections at the other times in this idealized example. If undergoing a periodic motion, the moving object 310 may return to its position at time T1, but his will not change the value of the stationary projection determined by the minimum operation.

The third column (column C) gives the difference between the original projection and the stationary projection at each time. This difference is called the motion projection hereinafter. At time T1 the minimum is the same as the original so there is no difference; but, at subsequent times the moving object that has been removed from the stationary projections in the second column now appears in the motion projections in the third column. These motion projection can be used individually, as described below, or summed to generate an image that depicts pixels subject to motion effects.

FIG. 3 assumes the moving object 310 moves more than its width in the illustrated projections and thus completely evacuates the original pixels during its motion. However, in other embodiments, a moving object may move a total distance less than its width in all the projections at a particular direction. In that case, the pixels not evacuated by the moving object retain some intensity from the moving object in the stationary projection.

FIG. 3 also assumes the moving object 310 has a higher pixel value than the average value or the background tissue and is removed in the minimum operation. However, in some embodiments, the moving object might be an air pocket or gas bubble that has a lower pixel value, or the actual received intensity is used instead of the analogous x-ray attenuation value so that the moving object 310 has a lower value than the average or surrounding tissue. In such embodiments, the minimum operation is replaced with a maximum operation that takes the maximum value among corresponding pixels in multiple projections. The stationary projection then comprises the maximum values, and the motion projection is computed by subtracting the individual projections from the maximum values in the stationary projection. Hereinafter, this operation is also called determining a difference between the stationary projection and the actual projections to get the motion projections.

The following notation is introduced to express minimum operation in mathematical form. The minimum operator Min{a,b} is defined to act on two image functions $S_a(x, y)$ and $S_b(x, y)$, such as projections P1(x,y) and P2(x,y) described above, on a pixel by pixel basis to obtain a third image function $S_{a,b}(x, y)$ according to Equation 1.

$$S_{a,b}=\text{Min}\{S_a, S_b\}=\text{Min}\{S_a(x,y); S_b(x,y)\} \qquad (1)$$

for $x=\{x_1, \ldots x_{max}\}$ and $y=\{y_1, \ldots y_{max}\}$

To compute the minimum over all projections, in some embodiments, the sequentially acquired series of images P1(x, y); P2(x, y) . . . Pn(x, y) are processed as they are acquired, e.g., as given in Equation 2.

$$P_{1,2} = \text{Min}\{P1, P2\} \quad (2)$$

$$P_{1\text{-}3} = \text{Min}\{P_{1,2}, P3\}$$

$$\ldots$$

$$S = P_{1\text{-}n} = \text{Min}\{P_{1\text{-}(n-1)}, Pn\}$$

Where the notation $P_{1\text{-}c}$ is introduced to indicate the output after processing all projections from P1 through Pc. $P_{1\text{-}n}$ is referred to as the stationary projection S. The remaining parts of the projections P1 through Pn are called the motion projections M1 through Mn as given by Equation 3.

$$M1 = P1 - S \quad (3)$$

$$M2 = P2 - S$$

$$\ldots$$

$$Mn = Pn - S$$

In some embodiment the maximum is used to define the stationary and motion projections, as given by Equations 4, 5 and 6.

$$S_{a,b} = \text{Max}\{S_a, S_b\} = \text{Max}\{S_a(x,y); S_b(x,y)\} \quad (4)$$

for $x=\{x_1, \ldots x_{max}\}$ and $y=\{y_1, \ldots y_{max}\}$

To compute the maximum over all projections, in some embodiments, the sequentially acquired series of images P1(x, y); P2(x, y) . . . Pn(x, y) are processed as they are acquired, e.g., as given in Equation 5.

$$P_{1,2} = \text{Max}\{P1, P2\} \quad (5)$$

$$P_{1\text{-}3} = \text{Max}\{P_{1,2}, P3\}$$

$$\ldots$$

$$S = P_{1\text{-}n} = \text{Max}\{P_{1\text{-}(n-1)}, Pn\}$$

The remaining parts of the projections P1 through Pn are called the motion projections M1 through Mn as given by Equation 6.

$$M1 = S - P1 \quad (6)$$

$$M2 = S - P2$$

$$\ldots$$

$$Mn = S - Pn$$

In some embodiments, the motion projections M1 through Mn are assembled into a video clip and displayed on a display as a series at corresponding times t1, t2 . . . tn. In some embodiments, the M1 through Mn are added together to produce a movement image which is displayed to indicate the pixels affected by movement. In some embodiments the M1 through Mn are grouped into a plurality of movement phases corresponding to different portions of a periodic movement, such as full inflate, full deflate, and one or more inhale and one or more exhale images, each called a motion phase image. In some embodiments, a corrected projection is computed and displayed by adding the motion phase image for one phase and the stationary projection S.

FIG. 4 is a flow diagram that illustrates an example method 400 for suppressing motion artifacts in an X-ray fluoroscopy projection, according to an embodiment. Although steps are depicted in FIG. 4, and in subsequent flowchart FIG. 6, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 401 the parameters of the method are initialized. In some embodiments, the parameters initialized include parameters that indicate n, xmax, ymax and set up data arrays P(xmax, ymax, n) for the projections P1 through Pn. Furthermore, in some embodiments, a data array S(xmax, ymax) to accumulate the stationary projection is initialized with values. For example, in some embodiments, a minimum pixel array to record the results of a minimum operation is initialized with a maximum value (e.g., 255) for each pixel so that any measured value is less than the initialized value. In some embodiments, a maximum pixel array to record the results of a maximum operation is initialized with a minimum value (e.g., 0) for each pixel so that any measured value is greater than the initialized value. Other parameters set during step 401 in various embodiments include a parameter indicating whether the imaging system is an x-ray fluoroscopy imager, a revolving X-ray CT imager, or a gamma ray imager. Another parameter used in some embodiments, indicates whether a moving object of interest is expected to have a higher pixel value than average or adjacent tissue or a lower pixel value, so it can be determined whether a minimum or maximum operation is appropriate. Another parameter in some embodiments, indicates what motion phases are associated with output ranges from the motion sensor 130.

In step 403, the values of pixels for the next projection at the detector, e.g., Pk saved as P(x,y,k), are obtained, as are data from the motion sensor 130. Thus, step 403 includes obtaining a plurality of projections, at a corresponding plurality of different times within a time interval, from a medical imaging system operating on a subject, wherein each projection comprises a plurality of pixel values, each pixel value corresponding to a value of a signal received at a component of a detector array from a signal source after the signal passes through the subject, and wherein an object of interest potentially inside the subject is expected to move during the time interval.

Step 403 also include obtaining output from the motion sensor. This sensor output is represented by the symbol Z, so that for all projections 1 through n, there are corresponding motion sensor measurements Z1 through Zn. The motion phases based on the output from the motion sensor are given by the motion phase function B, which is a function of the sensor output B(Z). The value of B can be continuous (e.g., a measured displacement) or discontinuous (e.g. constant at phase 1 for some duration then jumps to phase 2 for the next time duration, such as the greatest integer of a continuous measured displacement). If B is periodic with period τ, then so is Z, and B(Z(t))=B(Z(t+τ)). The H different values taken on by the function B are represented by the symbols β1 through βH, or simply βh, h=1 to H.

Any method may be used to obtain the projection and motion sensor data, including sending commands to an imaging system to collect the data, or retrieving previously collected data from a local or remote data storage device or database, or some combination.

In step 405, the stationary projection S is updated with the latest projection. The stationary projection S can be easily implemented in a computer program with instructions such as the following for a stationary projection defined by the minimum operation and initialized with S(x,y)=255 for all x and y.

```
For k = 1 to n
    For x = 1 to xmax
        For y = 1 to ymax
            S(x,y) = Min(S(x,y), P(x,y,k)).
```

This implements Equation 2, above. In other embodiments, the maximum is computed in addition to or instead of the minimum. In some embodiments, the determination of whether to store the maximum or minimum or both is based on a parameter directed to the pixel values of an object of interest, which is initialized in step 401 and described above. If the imaging system is an x-ray fluoroscope then all projections are associated with a first subset in which the source and receiver are in a first configuration, e.g., relative angle compared to the subject is fixed. If the imaging system is CT system with revolving source and detector array, then only one projection per revolution is associated with a first subset in which the source and receiver are in a first configuration, e.g., within a small range of angles of revolution. Thus, step 405 includes determining a stationary projection for a first subset of the plurality of projections, wherein the signal source and detector array are in a first configuration relative to the subject for the first subset of the plurality of projections.

In step 407, it is determined if all motion phases are covered, e.g., whether the series of projections have been performed for a sufficient duration of time to cover one or more periodic movement cycles (e.g., duration $>\tau$) or long enough to average out any non-periodic movements. If not, then control passes back to step 403 to obtain another projection and associated output from the motion detector. If enough projections have been accumulated, then control passes to step 409.

In step 409, it is determined whether the moving object of interest is expected to have a higher pixel value than average or adjacent tissue. If so, then a minimum operation is appropriate and control passes to step 411. If not, then a maximum operation is appropriate and control passes to step 421 instead. Thus step 409 includes, for any subset, determining that the stationary projection comprises a minimum value for each pixel of the plurality of pixels among the subset of the plurality of projections if a signal passing through the object of interest is expected to cause an increase in a pixel value, compared to a signal that does not. Similarly, step 409 includes determining that the stationary projection comprises a maximum value for each pixel of the plurality of pixels among the subset of the plurality of projections if the signal passing through the object of interest is expected to cause a decrease in a pixel value, compared to the signal that does not.

In step 411 the stationary projection is taken equal to the minimum pixel array, e.g., S as computed using the minimum function of Equation 2 as implemented in step 405. In step 413, the stationary projection S is subtracted from each measured projection P1 through Pn to get the motion projections at each time, M1 through Mn, according to Equation 3. Control then passes to step 431 described below.

In step 421 the stationary projection is taken equal to the maximum pixel array, e.g., S as computed using the maximum function of Equation 5 as implemented in step 405. In step 423, each measured projections P1 through Pn is subtracted from the stationary projection S to get the motion projections at each time, M1 through M,n according to Equation 6. Control then passes to step 431.

In step 431, in some embodiments, the motion projections M1 through Mn are sorted into groups according to several motion phases, e.g., different breathing phases. In step 433, in some embodiments, the motion projections in each motion phase are combined, e.g., averaged or added or used to compute a harmonic mean or combined in a weighted sum, to get a motion phase image for one or more phases. For example a full lung motion phase is determined by averaging all motion projections obtained during a full lung motion phase. In some embodiments, in step 435, the stationary projection is re-combined with one or more of the motion phase images computed in step 433, e.g., by adding the motion phase image to the stationary projection, to produce a corrected projection image for each phase. In some embodiments, motion projections are not grouped by motion phases; and, steps 431, 433 and 435 are omitted.

In step 437, an image is presented on a display device, such as a monitor, television, or printout on flat or photographic quality paper. Any of the images computed in the above steps may be presented, alone or in some combination, including the stationary projection, the motions projections (alone or in full or subsampled sequence, such as in a video clip), the motion phase image, or the corrected projection. In some embodiments, step 437 includes using the presented image, e.g., to diagnose a disease or good health, or to determine the progress of a disease, e.g., by tumor size, either when untreated or in response to some treatment or combination of treatments.

Thus step 437 includes presenting on a display device an image of the subject based on the stationary projection. For example, step 407 includes presenting the stationary projection, a motion image based on a difference between the stationary projection and a projection of the first subset of the plurality of projections, a motion phase image based on one or more motion images collected during a particular motion phase when the object of interest moves periodically through a plurality of motion phases, or a corrected image based on the motion phase image recombined with the stationary image.

Figures 5A, 5B, 5C:
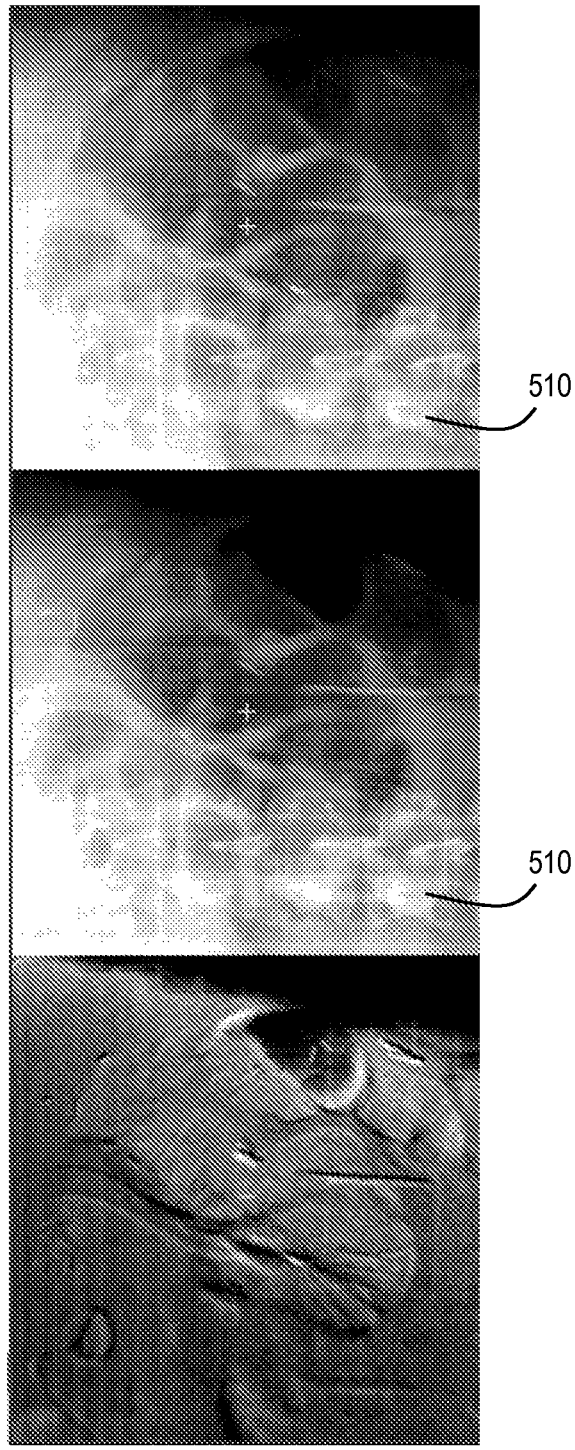
FIG. 5A through FIG. 5C are images that illustrate example images presented as a result of the method of FIG. 4, according to an embodiment.

FIG. 5A through FIG. 5C are images that illustrate example images presented as a result of the method of FIG. 4, according to an embodiment. FIG. 5A is an image of an example measured projection. Evident in the measured projection are white areas 510 that indicate bones of a spine of a subject. FIG. 5B is an image of the stationary projection from a series of measured projections. The white areas 510 of the stationary spine are still evident. FIG. 5C is an image of a motion projection obtained by the difference of the images of FIG. 5A and FIG. 5B. Note that the stationary spine is absent. Pixels that experience the biggest difference due to movement are white and pixels that are not different from the stationary image are black.

FIG. 6 is a flow diagram that illustrates an example method 600 for suppressing motion artifacts in CT images, according to an embodiment. Step 601 is similar to step 401 described above. The parameters initialized include a set of parameters that indicates how many different angles θ1 through θn are used in a fully sampled tomographic reconstruction, how many are desired as a minimum (e.g., want at least 20 angles for each motion phase), the rate of revolution 125, and what ranges of outputs from the motion sensor 130 constitutes a single motion phase βh and the total number H of motion phases. For example, if each 2 units of displacement in FIG. 2 is considered a different motion phase then there are 10 motion phases. If the motion phase at displacements near +/−10 are only one unit wide, then there are 11 motion phases. If inhale bins are distinguished from exhale bins in this same approach, then there are 20 motion phases. Thus, an object of interest potentially inside the subject, such as a tumor, gas pocket or gamma ray source, is expected to move during the time interval of projection measurements.

In step 603, the values of pixels for the next projection at the detector, e.g., Pk saved as P(x,y,k), are obtained, as are data Zk from the motion sensor 130. Each successive projection Pk is also obtained at a different angle θk and a different time tk with a corresponding movement phase B(Zk), the latter just called Bk for convenience hereinafter. Each different angle or small range of angles is considered a different configuration. If the projections associated with a particular configuration are considered a subset of all the data projections, then there are multiples configuration subsets with corresponding narrow angle ranges among the collected data. Any method may be used to obtain the projection and motion sensor data, including sending commands to an imaging system to collect the data, or retrieving previously collected data form a local or remote data storage device or database, or some combination.

Thus, step 603 includes obtaining a plurality of projections, at a corresponding plurality of different times within a time interval, from a medical imaging system operating on a subject, wherein each projection comprises a plurality of pixel values, each pixel value corresponding to a value of a signal received at a component of a detector array from a signal source after the signal passes through the subject. Furthermore, the plurality of projections are based on a corresponding plurality of different configurations of the signal source and detector relative to the subject.

In step 605, it is determined if there is another revolution angle at which to make a measurement, e.g., it is determined whether the revolution has completed 360 degrees. If not, control passes back to step 603 to obtain another projection. For example, if k<n, then control passes back to step 603. If the current revolution is completed, then control passes to step 607. In step 607 the number of different angles for each motion phase is determined. If this number is less than the minimum desired, e.g., 20, as determined by a parameter set in step 601, then control passes back to step 603 to obtain data from another revolution. If a sufficient number of different angles/configurations are available for each motion phase, then control passes to step 611. In some embodiments, step 607 is omitted and data from a single revolution is used; so, control passes directly from step 607, no branch, to step 611.

In step 611 the projections are sorted into motion phases. For example about 600 projections are sorted into 20 motion phases for an average of about 30 configurations per motion phase, although some motions phases have much less and others much more. As another example, about 600 projections are sorted into 10 motion phases, averaging twice as many projections per motion phase. In some embodiments, step 607, if present, follows step 611. For any one configuration of source and receiver (e.g., for one angle of revolution θk) during a single revolution, there is only one projection Pk and only one motion phase Bk. However, for any motion phase B (e.g., B=5 in FIG. 2) there are multiple different configurations (angles) of source and receiver relative to the subject available (e.g., θ3, θ12, θ19, θ33, etc. in FIG. 2), each with a corresponding projection (e.g., P3, P12, P19, P33, etc.). These multiple configurations can be used to reconstruct a motion phase specific but undersampled tomographic slice.

In step 621, a fully sampled computed tomographic slice is reconstructed using all projections, e.g., all 600 projections for the example embodiment of FIG. 2. That is, the Pk, θk are used with the inverse Radon transform, to produce an initial CT slice $I_0(i, j)$. This is given by Equation 7, where R indicates the Radon transform and $R^{-1}$ indicates the inverse Radon transform.

$$I_0(i,j)=R^{-1}(Pk,\theta k, k=1,n) \quad (7)$$

This slice has blurred portions where motion of one or more objects has caused motion artifacts. Thus step 621 includes determining a computed tomography image directly based on the plurality of projections.

In step 623 the blurred CT slice I0 of step 621 is used to compute digitally reconstructed projections F(x,y) (also called digitally reconstructed radiographs, DDR) for each of the configurations indicated by the angles θk, k=1, n, e.g., using the forward Radon transform denoted by the symbol R, as given in Equation 8.

$$F1(x, y) = R(I_0(i, j), \theta 1) \quad (8)$$
$$F2(x, y) = R(I_0(i, j), \theta 2)$$
$$\ldots$$
$$Fn(x, y) = R(I_0(i, j), \theta n)$$

Fk is not the same as Pk, because Pk is based on the actual distribution of density $f$ (e.g., X-ray attenuation or gamma ray intensity or attenuation) at time tk, while Fk is based on some blurred average arrangement of the density $f$ over the entire collection interval. Thus step 623 includes determining a plurality of digitally reconstructed projections (Fk, k=1, n) based on the computed tomography image $I_0(i,j)$, each digitally reconstructed projection Fk based on one of the plurality of different configurations θk.

In step 625, a stationary projection Sk at each angle is computed based on the digitally reconstructed projection Fk and the measured projection Pk by taking the appropriate minimum or maximum, as determined based on the parameters set in step 601. For example, if the minimum is appropriate, then Equation 9a is used.

$$Sk=\text{Min}\{Fk,Pk\} \text{ for } k=1,n \quad (9a)$$

Similarly if the maximum is appropriate, then Equation 9b is used.

$$Sk=\text{Max}\{Fk,Pk\} \text{ for } k=1,n \quad (9b)$$

Thus, step 625 includes determining a plurality of stationary projections Sk, k=1,n; each Sk based on both a digitally reconstructed projection Fk of the plurality of digitally reconstructed projections and a projection Pk of the plurality of projections for a corresponding configuration θk of the plurality of different configurations.

In step 627, a stationary computed tomography (CT) slice $I_S(i,j)$ is computed from the stationary projections Sk, k=1, n. That is, the Sk, θk are used with the inverse Radon transform, to produce an stationary CT slice $I_S(i, j)$. Thus, step 627 includes determining a stationary computed tomography image based on the plurality of stationary projections.

In step 629, it is determined whether the stationary CT slice is acceptable. For example, it is acceptable if it is smooth without spurious lines crossing at different direction, as is common with motion artifacts. If not, control passes back to repeat steps 623 through 627 to produce an iterated set of digitally reconstructed projections, Fk' based on the $I_S(i,j)$ instead of the $I_0(i, j)$. These are used with the Pk, to produce an iterated set of stationary projections Sk', which are used to produce an iterated stationary CT slice $I_S'(i,j)$ which is tested again in step 629 for acceptability. If not acceptable again, control passes back to repeat steps 623 through 627 to produce a twice iterated set of digitally reconstructed projections, Fk" based on the $I_S'(i,j)$ instead of the $I_S(i, j)$. These are used with the Pk, to produce a twice iterated set of stationary projections Sk", which are used to produce a twice iterated stationary CT slice $I_S''(i,j)$ which is tested again in step 629 for acceptability. The steps 623 through 629 are repeated until the stationary CT slice is found acceptable or no longer improving. This accepted version of the stationary CT slice is designated $I_S^*(i, j)$ and the corresponding digitally reconstructed projections are designated Fk*(x,y) and the final set of stationary projections are designated Sk*(x,y). Then control passes to step 631.

In step 631, the final set of stationary projections Sk*(x,y) for k=1, n are used to determine a difference from the measured projections Pk(x,y) for k=1, n to produce the motion projections Mk(x,y) according to Equations 10a or 10b. Where the minimum is appropriate the difference is defined as in Equation 10a $$M1 = P1 - S1^*$$
$$M2 = P2 - S2^*$$
$$\ldots$$
$$Mn = Pn - Sn^*$$
(10a)

Where the maximum is appropriate, the difference is defined as in Equation 10b.

$$M1 = S1^* - P1$$
$$M2 = S2^* - P2$$
$$\ldots$$
$$Mn = Sn^* - Pn$$
(10b)

Thus step 631 includes a motion projection based on a difference between a projections of the plurality of projections and a corresponding stationary projection of the plurality of stationary projections.

These motion projections are then grouped into different motion phases when the object of interest moves periodically through a plurality of motion phases. Let the motion phase B take on one of H different Values, β1, β2, ... βL (e.g., H=10 when inhale and exhale displacements are not distinguished). Let {b1} indicate the members of the set {1, ..., n} associated with a particular motion phase B=β1, e.g., {b1}={2, 12, 19, 33, ...}, etc., and, in general, let {bh} indicate the members associated with motion phase B=βh. Then the motion projections for motion phase βh are designated Mh, h∈{bh}.

In step 633 the motion computed tomography (CT) slice (MIh) for a current phase βh is determined using the inverse Radon transform and the Mh and associated θh, as given by Equation 11.

$$MI_h(i,j)=R^{-1}(Mh,\theta h, \text{for all } h=\{bh\})$$
(11)

Thus step 633 includes determining a motion phase tomography image based only on a plurality of motion projections, each motion projection based on a difference between a projection of the plurality of projections and a corresponding stationary projection of the plurality of stationary projections, wherein each motion projection in the plurality of motion projections occurs during the particular motion phase.

In step 635, the motion CT slice for the current phase $MI_h(i,j)$ is combined with the stationary CT slice $I_S^*(i, j)$ to get a corrected CT slice for the current phase, designated CIh(i,j), according to Equation 12.

$$CIh(i,j)=I_S^*(i,j)+MI_h(i,j)$$
(12)

Thus, step 635 includes determining a corrected tomography image based on the motion phase tomography image recombined with the stationary computed tomography image. In step 637 it is determined whether there is another motion phase to process, e.g., whether h<H. If so, control passes back to step 631 to repeat steps 631, 633,635 for the next motion phase. If instead, all motion phases have been processed, and h=H, then control passes to step 641.

In step 641, one or more of the stationary projections, or the stationary CT slice, or the motion projections, or the motion CT slices for various motion phases, or the corrected CT slices for the various phases are presented on a display device. Thus, step 641 includes presenting an image of the subject based on the stationary computed tomography image. In some embodiments, step 641 includes using the presented image, e.g., to diagnose a disease or good health, or to determine the progress of a disease, e.g., by tumor size, either when untreated or in response to some treatment or combination of treatments.

2. Example Embodiments

The efficacy of the method was tested by simulating a simple 2D+time respiratory phantom. Feasibility was demonstrated by comparing a simple filtered back-projection algorithm, currently in use, along with the proposed motion suppression method 600 of FIG. 6 to reconstruct 2D+time images. The core of the technique rests on separating out the motion components from individual projection data by selecting the minimum (or maximum) intensity between projections and digitally reconstructed projections. This information is then later added back into the final images reconstructed at each individual phase to suppress motion artifacts.

Figure 7A:
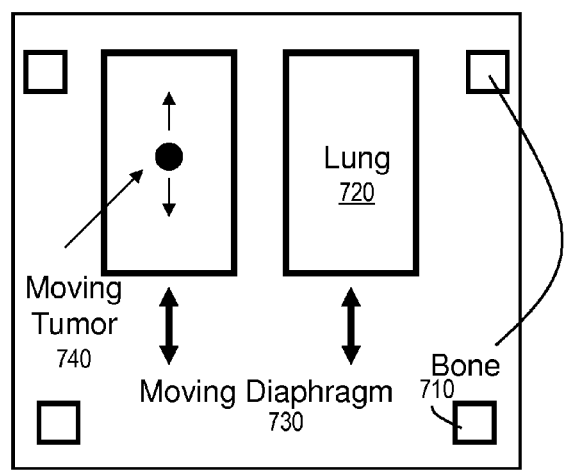
FIG. 7A is a block diagram that illustrates an example lung phantom model to simulate motion artifacts suppression, according to an embodiment.

FIG. 7A is a block diagram that illustrates an example lung phantom model to simulate motion artifacts suppression, according to an embodiment. The simulation is entirely numerical and is based on simulating the attenuation of a parallel X-ray beam between a source and line detector that revolve 360 degrees around the phantom. The pencil beam source moves in a parallel motion with respect to the straight line of detectors to generate the projection data, and this is repeated at each of the source-detector assembly angles within one revolution. The detector array is an idealized single-row detector bank. The phantom includes a square area of average tissue providing a medium attenuation background in which are inserted four areas of bones 710 that completely block x-rays and therefore have high attenuation, two areas of lung tissue 720 with lower attenuation than the background tissue, and a circular tumor 740 with higher attenuation than the lung tissue and roughly centered in the left lung as viewed on the page. The lungs periodically shrink and expand in length from the bottom, simulating breathing motion of a diaphragm 730, and the tumor 740 moves proportionately in the left lung. The diaphragm motion due to breathing is steady and periodic in the simulation and is plotted in the graph of FIG. 2. Also plotted in FIG. 2 are the angles at which a projection is computed over the first 100 degrees of the 360 degrees of a complete revolution.

Figure 7B:
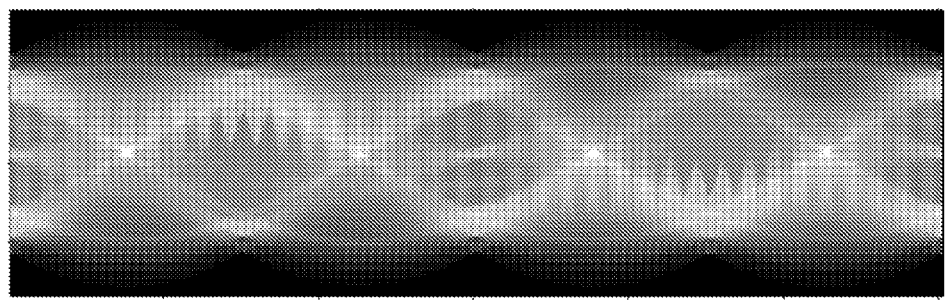
FIG. 7B is an image that represents a time series of one dimensional projections (sinogram) during one revolution of a simulated x-ray source and detector array, and 36 breathing cycles, according to an embodiment.

FIG. 7B is an image that represents a time series of one dimensional projections (sinogram) during one revolution of a simulated x-ray source and detector array, and 36 breathing cycles, according to an embodiment. Each vertical strip represents a one dimensional projection from one pointing (central) angle of the fan beam source. Thus the projections Pk are one dimensional, e.g., functions of x, not y, and expressed as Pk(x). Time (and index k) increases to the right. The breathing cycle is evident as 36 dark stripes or sawtooth peaks evenly distributed through the sinogram. Each of the four bones contributes one white sine curve that completes one cycle across the sinogram from left to right, indicating one revolution of the source and detector. The sinogram of FIG. 7B represents the raw data available for computed tomography obtained during step 603 of the method 600 in FIG. 6. The data obtained from the motion sensor during step 603 is simulated by the trace 206 in FIG. 2. These data are used with steps of the method 600 of FIG. 6 to produce the motion separated images presented hereinafter.

Figure 8A:
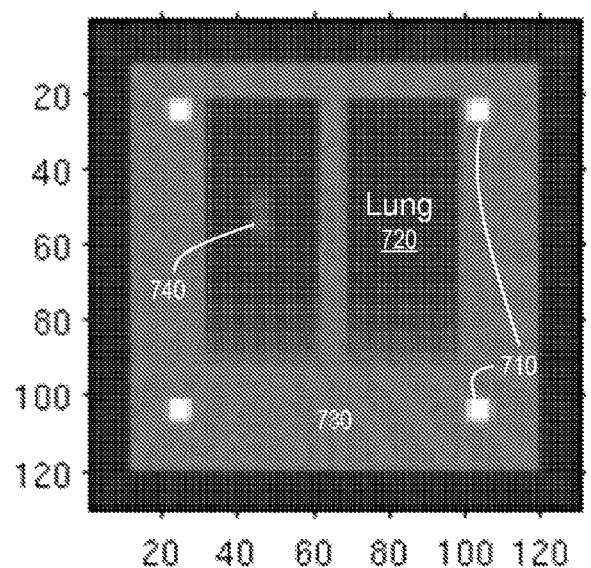
FIG. 8A is a block diagram that illustrates an example computed tomography slice based on all projections in FIG. 7B, according to an embodiment.

FIG. 8A is a block diagram that illustrates an example computed tomography slice based on all projections in FIG. 7B, according to an embodiment. This correspond to $I_0(i,j)$ computed using Equation 7 during step 621. The bones 710 are rather well defined, but the tumor 740 and bottom of the lungs 720 are blurred due to the simulated motion of a diaphragm 730.

Figure 8B:
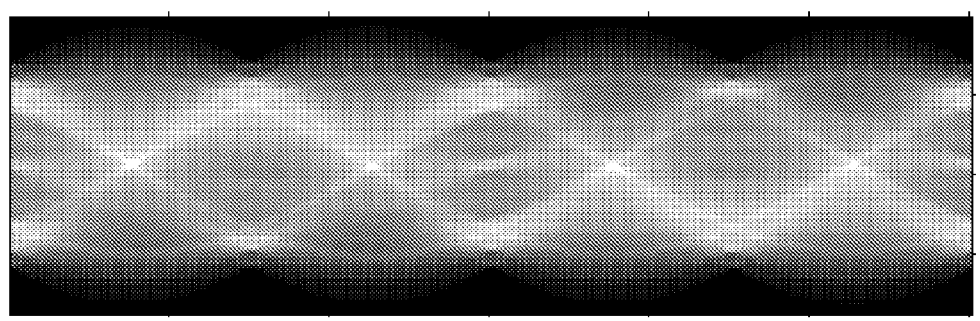
FIG. 8B is an image that represents a time series of one dimensional digitally reconstructed projections through the slice of FIG. 8A during same revolution, according to an embodiment.

FIG. 8B is an image that represents a time series of one dimensional digitally reconstructed projections through the slice of FIG. 8A during the same revolution, according to an embodiment. Each vertical strip represents one 1D digitally reconstructed projection, Fk(x) for each angle θk, as computed by each line of Equation 8 during step 623 if ymax=1. The breathing cycle has been blurred out of the sinogram.

During step 625 the stationary projections Sk are determined by taking the minimum at each pixel of the two values available form FIG. 7B and FIG. 8B. The resulting sinogram is not shown. Those stationary projections are used to compute a stationary tomographic image (slice), also not shown, which is improved upon by repeating for several iterations to produce the final stationary tomographic image $I_S^*$. While 3 iterations were used in the simulation, it is anticipated that similar results can be achieved with just 2 iterations in the simplified geometry presented in this embodiment.

Figure 8C:
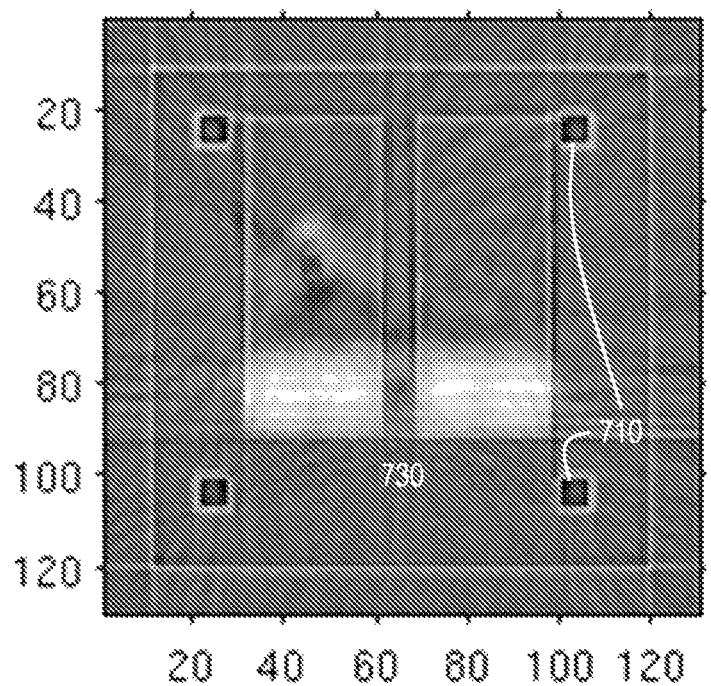
FIG. 8C is an image that illustrates an example motion computed tomography slice based on a difference between all the projections from FIG. 7B and corresponding stationary projections in one motion phase, according to an embodiment.

In step 631, the final set of stationary projections Sk*(x) for k=1, n are used to difference from the measured projections Pk(x) for k=1, n to produce the motion projections Mk(x) according to Equations 10a. These are then grouped by motion phase and in step 633 used to compute a motion tomographic slice $MI_h(i,j)$ for each motion phase h=1, H. Of these, the motion phase associated with the most motion, e.g., at full inhale, is presented in FIG. 8C. FIG. 8C is an image that illustrates an example motion computed tomography slice based on a difference between all the projections from FIG. 7B and corresponding stationary projections in one motion phase, according to an embodiment. Great motion is associated with the lower lungs near diaphragm 730, almost no motion is associated with the bones 710, and the next amount of motion around an average position for the tumor.

FIG. 9A is a set of three images showing left to right the example lung phantom model during one motion phase (131), an example under-sampled computed tomography slice using only projections during that motion phase as used in current algorithms, and an example computed tomography slice for the same motion phase using the method 600 of FIG. 6, which uses a stationary computed tomography slice based on all projections, respectively, according to an embodiment. FIG. 9B and FIG. 9C are like FIG. 9A but for two different motion phases β5 and β9, respectively, according to an embodiment. Due to the severe under sampling at certain phases (e.g., phase β35, where only 37 projections were acquired out of 602 projections), the results from undersampled reconstruction have severe motion related artifacts. These however are substantially suppressed using the proposed method 600 to produce the corrected slices per phase, CIh(i,j) as computed in step 635 and depicted in the last column. Similarly, the method also reduces geometric distortions that may result from selective angular sampling as is apparent in the images acquired at Phase β5.

Thus, the technique has been demonstrated on a 2-dimensional simulated moving lung phantom. Initial results on this 2D+time simulated phantom proves that severe under-sampling artifacts can be eliminated and individual phase images can be reconstructed with high fidelity when compared to standard under-sampled filtered back-projection (second column of FIG. 9A through FIG. 9C).

3. Hardware Overview

FIG. 10 is a block diagram that illustrates a computer system 1000 upon which an embodiment of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of one or more methods described herein.

A sequence of binary digits constitutes digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information. The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitute computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1070 sends and receives electrical, acoustic or electromagnetic signals, including infrared and optical signals, that carry information streams, such as digital data.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1002, except for carrier waves and other signals.

Logic encoded in one or more tangible media includes one or both of processor instructions on a computer-readable storage media and special purpose hardware, such as ASIC 1020.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

The invention is related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1008. Execution of the sequences of instructions contained in memory 1004 causes processor 1002 to perform the method steps described herein. In alternative embodiments, hardware, such as application specific integrated circuit 1020, may be used in place of or in combination with software to implement the invention. Thus, embodiments of the invention are not limited to any specific combination of hardware and software.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a signal on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

Figure 11:
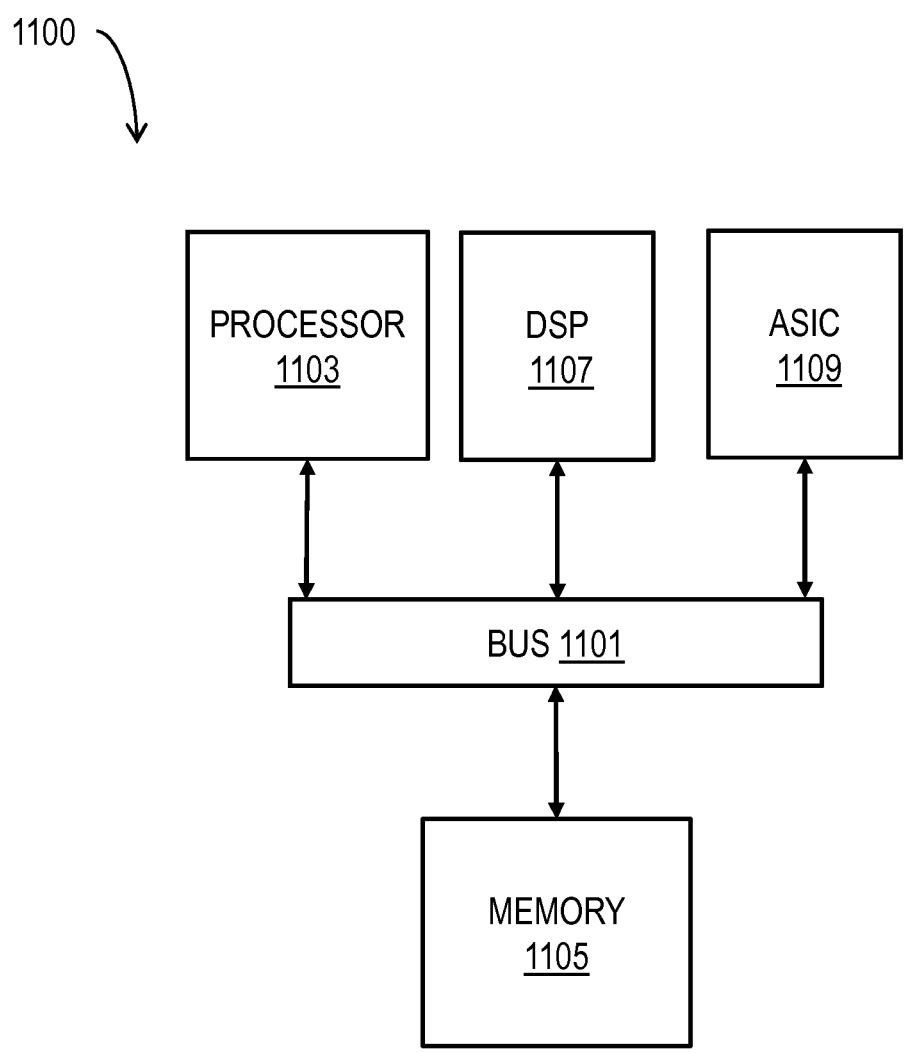
FIG. 11 illustrates a chip set upon which an embodiment of the invention may be implemented.

FIG. 11 illustrates a chip set 1100 upon which an embodiment of the invention may be implemented. Chip set 1100 is programmed to perform one or more steps of a method described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of a method described herein.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1105 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A non-transitory computer-readable medium carrying one or more sequences of instructions, wherein execution of the one or more sequences of instructions by one or more processors causes an apparatus to perform the steps of:

obtaining a plurality of projections, at a corresponding plurality of different times within a time interval, from a medical imaging system operating on a subject, wherein each projection comprises a plurality of pixels, wherein each pixel has a location and a value, each pixel value corresponding to a value of a signal received at a component of a detector array from a signal source after the signal passes through the subject and the location of each pixel is the same as a location of the component of the detector array, and wherein an object of interest potentially inside the subject is expected to move during the time interval;

determining a stationary projection for a first subset of the plurality of projections, wherein the signal source and detector array are in a first configuration relative to the subject for the first subset of the plurality of projections;

determining a motion projection based on a difference between a projection of the plurality of projections and the stationary projection; and presenting on a display device an image of the subject based on the stationary projection or the motion projection or both, wherein, for any subset:

the stationary projection comprises a minimum value for each pixel of the plurality of pixels among the subset of the plurality of projections if a signal passing through the object of interest is expected to cause an increase in a pixel value, compared to a signal that does not; and the stationary projection comprises a maximum value for each pixel of the plurality of pixels among the subset of the plurality of projections if the signal passing through the object of interest is expected to cause a decrease in a pixel value, compared to the signal that does not.

2. A non-transitory computer-readable medium as recited in claim 1, wherein:

the signal source is an X-ray source; and the value of the signal received at the component of the detector array indicates attenuation of the X-rays from the X-ray source.

3. A non-transitory computer-readable medium as recited in claim 2, wherein:

the object of interest is a tumor; and the signal passing through the object of interest is expected to cause an increase in a pixel value.

4. A non-transitory computer-readable medium as recited in claim 1, wherein:

the object of interest is a gas pocket; and the signal passing through the object of interest is expected to cause a decrease in a pixel value.

5. A non-transitory computer-readable medium as recited in claim 1, wherein presenting the image of the subject based on the stationary projection comprises presenting at least one of:

the stationary projection;

wherein the motion projection is a first motion projection based on a difference between the stationary projection and a projection of the first subset of the plurality of projections;

a motion phase image based on one or more first motion projections collected during a particular motion phase when the object of interest moves periodically through a plurality of motion phases; or a corrected image based on the motion phase image recombined with the stationary image.

6. A non-transitory computer-readable medium as recited in claim 5, wherein the plurality of motion phases are a plurality of phases associated with breathing by the subject.

7. A non-transitory computer-readable medium as recited in claim 6, wherein the plurality of projections are based on a corresponding plurality of different configurations of the signal source and detector relative to the subject;

wherein the apparatus is further caused to perform the steps of:

determining a computed tomography image directly based on the plurality of projections;

determining a plurality of digitally reconstructed projections based on the computed tomography image, each digitally reconstructed projection based on one of the plurality of different configurations;

determining a plurality of stationary projections, each based on both a digitally reconstructed projection of the plurality of digitally reconstructed projections and a projection of the plurality of projections for a corresponding configuration of the plurality of different configurations; and determining a stationary computed tomography image based on the plurality of stationary projections; and wherein presenting an image of the subject further comprises presenting an image of the subject based on the stationary computed tomography image.

8. A non-transitory computer-readable medium as recited in claim 7, wherein presenting the image of the subject based on the stationary projection comprises presenting at least one of:

the stationary computed tomography image;

wherein the motion projection is a second motion projection based on a difference between a projection of the plurality of projections and a corresponding stationary projection of the plurality of stationary projections;

a motion phase tomography image when the object of interest moves periodically through a plurality of motion phases, wherein the motion phase tomography image is based only on a plurality of second motion projections, each second motion projection based on a difference between a projection of the plurality of projections and a corresponding stationary projection of the plurality of stationary projections, wherein each second motion projection in the plurality of second motion projections occurs during the particular motion phase; and a corrected tomography image based on the motion phase tomography image recombined with the stationary computed tomography image.

9. A non-transitory computer-readable medium as recited in claim 8, wherein the plurality of motion phases are a plurality of phases associated with breathing by the subject.

10. A non-transitory computer-readable medium as recited in claim 1, wherein:

the signal source is a gamma source disposed within the subject; and the value of the signal received at the component of the detector array indicates number of a gamma photons from the gamma source.

11. An apparatus comprising:

a display device;

at least one processor; and at least one memory including one or more sequences of instructions, the at least one memory and the one or more sequences of instructions configured to, with the at least one processor, cause the apparatus to perform at least the following, obtain a plurality of projections, at a corresponding plurality of different times within a time interval, from a medical imaging system operating on a subject, wherein each projection comprises a plurality of pixels, wherein each pixel has a location and a value, each pixel value corresponding to a value of a signal received at a component of a detector array from a signal source after the signal passes through the subject and the location of each pixel is the same as a location of the component of the detector array, and wherein an object of interest potentially inside the subject is expected to move during the time interval;

determine a stationary projection for a first subset of the plurality of projections, wherein the signal source and detector array are in a first configuration relative to the subject for the first subset of the plurality of projections;

determine a motion projection based on a difference between a projection of the plurality of projections and the stationary projection; and present on the display device an image of the subject based on the stationary projection or the motion projection or both, wherein, for any subset:
the stationary projection comprises a minimum value for each pixel of the plurality of pixels among the subset of the plurality of projections if a signal passing through the object of interest is expected to cause an increase in a pixel value, compared to a signal that does not; and the stationary projection comprises a maximum value for each pixel of the plurality of pixels among the subset of the plurality of projections if the signal passing through the object of interest is expected to cause a decrease in a pixel value, compared to the signal that does not.

12. An apparatus as recited in claim 11, wherein presenting the image of the subject based on the stationary projection comprises presenting at least one of:
the stationary projection;
wherein the motion projection is a first motion projection based on a difference between the stationary projection and a projection of the first subset of the plurality of projections;
a motion phase image based on one or more first motion projections collected during a particular motion phase when the object of interest moves periodically through a plurality of motion phases; or
a corrected image based on the motion phase image recombined with the stationary image.

13. An apparatus as recited in claim 11,
wherein the plurality of projections are based on a corresponding plurality of different configurations of the signal source and detector relative to the subject;
wherein the apparatus is further caused to:
determine a computed tomography image directly based on the plurality of projections;
determine a plurality of digitally reconstructed projections based on the computed tomography image, each digitally reconstructed projection based on one of the plurality of different configurations;
determine a plurality of stationary projections, each based on both a digitally reconstructed projection of the plurality of digitally reconstructed projections and a projection of the plurality of projections for a corresponding configuration of the plurality of different configurations; and
determine a stationary computed tomography image based on the plurality of stationary projections; and
wherein to present an image of the subject further comprises presenting an image of the subject based on the stationary computed tomography image.

14. An apparatus as recited in claim 13, wherein presenting the image of the subject based on the stationary projection comprises presenting at least one of:
the stationary computed tomography image;
wherein the motion projection is a second motion projection based on a difference between a projection of the plurality of projections and a corresponding stationary projection of the plurality of stationary projections;
a motion phase tomography image when the object of interest moves periodically through a plurality of motion phases, wherein the motion phase tomography image is based only on a plurality of second motion projections, each second motion projection based on a difference between a projection of the plurality of projections and a corresponding stationary projection of the plurality of stationary projections, wherein each second motion projection in the plurality of second motion projections occurs during the particular motion phase; and
a corrected tomography image based on the motion phase tomography image recombined with the stationary computed tomography image.

15. An apparatus as recited in claim 14, wherein the plurality of motion phases are a plurality of phases associated with breathing by the subject.

16. A system comprising:
the apparatus as recited in claim 11; and
the medical imaging system comprising the detector array and the signal source.

17. A system as recited in claim 16, wherein: the signal source is one of an X-ray fluoroscope source, a fan beam X-ray source, or a cone-beam X-ray source: and, the detector array is an X-ray detector array.

18. A system as recited in claim 17, wherein:
the object of interest is a tumor; and
the signal passing through the object of interest is expected to cause an increase in a pixel value.

19. A system as recited in claim 17, wherein:
the object of interest is a gas pocket; and
the signal passing through the object of interest is expected to cause a decrease in a pixel value.

20. A system as recited in claim 16, wherein: the signal source is one of a Positron Emission Tomography (PET) gamma ray source or a Single-Photon Emission Computed Tomography (SPECT) gamma ray source; the signal source is configured to be injected into the subject; and, the detector array is a gamma ray detector array.

* * * * *